(12) United States Patent
Hammond et al.

(10) Patent No.: US 11,173,172 B2
(45) Date of Patent: Nov. 16, 2021

(54) SKIN BARRIER COMPOSITION

(71) Applicant: HYPHENS PHARMA PTE. LTD., Singapore (SG)

(72) Inventors: Kevin Hammond, Wirral (GB); Adrian Davis, Dorking (GB)

(73) Assignee: HYPHENS PHARMA PTE. LTD., Singapore (SG)

( * ) Notice: Subject to any disclaimer, the term of this patent is extended or adjusted under 35 U.S.C. 154(b) by 0 days.

(21) Appl. No.: 16/611,529

(22) PCT Filed: May 10, 2018

(86) PCT No.: PCT/GB2018/051262
§ 371 (c)(1),
(2) Date: Nov. 7, 2019

(87) PCT Pub. No.: WO2018/206962
PCT Pub. Date: Nov. 15, 2018

(65) Prior Publication Data
US 2020/0222438 A1   Jul. 16, 2020

(30) Foreign Application Priority Data
May 10, 2017   (GB) ...................................... 1707489

(51) Int. Cl.
| | |
|---|---|
| *A61K 31/7032* | (2006.01) |
| *A61K 31/164* | (2006.01) |
| *A61K 31/191* | (2006.01) |
| *A61K 33/30* | (2006.01) |
| *A61K 47/10* | (2017.01) |
| *A61K 47/14* | (2017.01) |
| *A61K 9/00* | (2006.01) |
| *A61K 31/201* | (2006.01) |
| *A61K 31/365* | (2006.01) |
| *A61K 31/575* | (2006.01) |
| *A61K 9/06* | (2006.01) |

(52) U.S. Cl.
CPC ........ *A61K 31/7032* (2013.01); *A61K 9/0014* (2013.01); *A61K 31/164* (2013.01); *A61K 31/191* (2013.01); *A61K 31/201* (2013.01); *A61K 31/365* (2013.01); *A61K 31/575* (2013.01); *A61K 33/30* (2013.01); *A61K 47/10* (2013.01); *A61K 47/14* (2013.01); *A61K 9/06* (2013.01)

(58) Field of Classification Search
CPC .. A61K 31/7032; A61K 33/30; A61K 31/164; A61K 31/201; A61K 31/575; A61K 31/365; A61K 31/191; A61K 47/14; A61K 9/0014; A61K 47/10; A61K 9/06
USPC .......................................................... 514/53
See application file for complete search history.

(56) References Cited

U.S. PATENT DOCUMENTS

| | | | |
|---|---|---|---|
| 6,335,023 B1 | 1/2002 | Yu et al. | |
| 2002/0119174 A1 | 8/2002 | Gardlik et al. | |
| 2010/0069338 A1 | 3/2010 | Ward et al. | |
| 2015/0024074 A1* | 1/2015 | Batchvarova | ........ A61K 31/575 424/725 |

* cited by examiner

*Primary Examiner* — Yih-Horng Shiao
(74) *Attorney, Agent, or Firm* — Burns & Levinson, LLP; Daniel W. Clarke

(57) ABSTRACT

The present invention provides a composition for topical administration of a polyhydroxy acid, such as lactobionate and especially zinc lactobionate, and low pH to an external body surface such as skin. The composition is designed to be highly effective in delivering low pH and zinc lactobionate across the layers of the skin to more effectively treat and prevent skin conditions involving a defective skin barrier such as eczema and severe dry skin.

34 Claims, 10 Drawing Sheets

SKIN BARRIER COMPOSITION

RELATED APPLICATIONS

This application is a national stage application, filed under 35 U.S.C. § 371, of International Application No. PCT/GB2018/051262, filed May 10, 2018, which claims the benefit of priority under 35 U.S.C. § 119(e) to Great Britain Application No. 1707489.9, filed May 10, 2017, each of which is incorporated herein by reference in its entirety.

BACKGROUND

A defective skin barrier underlies a large range of conditions negatively affecting skin. For example, eczema and dermatitis are chronic skin conditions characterised by a defective skin barrier in which sufferers have dry, red and itchy skin. This can lead to cracked, sore skin and to eczematous lesions, particularly during a flare up of the condition. As such, eczema and dermatitis have significant psychological and sociological effects on both sufferers and their families.

It is estimated that 15-20% of children worldwide suffer from these conditions and incidence of these conditions are on the increase. Whilst some children outgrow these skin conditions, about 30-40% of individuals continue to suffer as adults. Therefore the current market for products treating eczema and dermatitis is more than £2 billion annually and growing. Estimates of the current market size for products capable of addressing all conditions caused by a defective skin barrier are not available, but are expected to be much higher.

Skin conditions such as eczema and dermatitis are complex, multifactorial conditions, including both genetic and environmental elements. A defective skin barrier involves a breakdown of the stratum corneum layer of the skin, a reduction in the cell to cell adhesion of the cells in the stratum corneum, and a thinning of the stratum corneum layer due to both compression of the corneocytes and increased loss of skin cells (desquamation) or a perturbation of the acid mantle. Furthermore, affected skin has reduced natural moisturising factor (NMF), reduced lamellar lipids, abnormally elevated skin protease activity and abnormally elevated skin pH.

A defective skin barrier allows greater loss of water across the skin and the penetration of environmental triggers such as allergens, irritants and toxins that can trigger a flare up of these skin conditions.

One type of existing treatment for conditions caused by a defective skin barrier includes emollient creams which can temporarily enhance the skin barrier function by providing a barrier to penetration of irritants, allergens and toxins and reducing water loss from the skin. However, they don't address the underlying biochemical imbalances and require frequent application.

Another type of existing treatment for conditions caused by a defective skin barrier includes medicated creams which can deliver anti-inflammatory, anti-allergenic and anti-itch benefits. However, they can lead to further skin thinning, dilation of blood vessels, increased skin fragility and increased risk of infection. These can ultimately mean a skin prone to a greater number of flare ups.

A further type of treatment involves creams or lotions comprising alpha hydroxy acids such as lactic acid and having a low pH. However, they frequently cause irritation or a stinging sensation when applied to affected skin and this leads to low patient compliance.

More recently treatments involving creams or lotions comprising polyhydroxy acids such as lactobionic acid have been developed. Creams or lotions based on these acids appeared to be milder and generally did not have the same issues of irritation and stinging. However, they failed to provide the hoped for efficacy in treating and preventing conditions caused by a defective skin barrier or in promoting repairing of a defective skin barrier.

Patients prefer a skin care treatment that they only need to apply a few times a day, and preferably only twice a day, as this is more convenient than multiple, frequent applications. Additionally patients prefer a skin care treatment that feels nice to use. If a skin care composition is less pleasant or less easy to use, for example because it is thick and greasy, or because it leaves an unsightly residue, or because of irritation on application, then patients will use it less regularly. A skin care formulation that is more pleasant to use leads to better patient compliance and a better outcome.

There remains an unmet need for an effective treatment for conditions involving a defective skin barrier, such as eczema, dermatitis and severe dry skin, which can treat and prevent such conditions and promote skin barrier repair, whilst being pleasant to use.

SUMMARY OF INVENTION

As noted above, creams or lotions for treating conditions such as eczema or dermatitis which include lactic acid, and depending on the concentration of lactic acid and its pH, cause irritation or a stinging sensation when applied to affected skin. Newer formulations involving polyhydroxy acids like lactobionic acid initially appeared to be an improvement since they caused less irritation and reduced stinging sensations. However, the effectiveness of such treatments also appears to be reduced. The present inventors hypothesized that the apparent reduction in efficacy of treatment noted for compositions containing lactobionic acid was due to inefficient delivery of this molecule because it is much larger than lactic acid, a molecular feature which works to reduce skin penetration. Therefore, the present invention provides a composition capable of improved delivery of polyhydroxy acids such as lactobionic acid and of low pH to the skin. It was unknown whether increased delivery of lactobionic acid, if increased delivery were to be achievable, would lead to the skin irritation and stinging associated with lactic acid. The present inventors have now provided a composition with improved delivery of a polyhydroxy acid such as lactobionic acid and low pH to the skin that surprisingly does not cause irritation or stinging, which would have been expected from effective delivery of an acid to skin having a defective skin barrier.

The present invention provides a composition for topical administration of a polyhydroxy acid and low pH to an external body surface such as skin, hair or nails. The composition of the present invention is designed to enhance flux across the skin and into the layers of the stratum corneum of the polyhydroxy acid and of the low pH, to effectively treat and prevent skin conditions involving a defective skin barrier and to help repair a defective skin barrier, whilst being non-irritant and pleasant to use. Therefore the present invention provides a skin barrier repair cream.

The present inventors have for the first time provided a composition for topical administration to an external body surface that provides all of the following benefits:

1) a sustained (up to 12 hours) reduction of skin surface pH relative to no treatment, 2) pH reduction that is not merely at the surface of the skin, but is also driven deep into the layers of the stratum corneum,
3) non-irritant and does not cause a stinging sensation in use despite having a low pH,
4) readily absorbed into the skin and feels nice to use,
5) causes inhibition of skin protease enzymes,
6) has an antibacterial effect, and
7) is stable on storage.

In contrast, prior to the present invention, skin care formulations did not provide all of these benefits and/or were less effective with respect to one or more aspects.

In a first aspect the present invention provides a composition for topical administration to an external body surface comprising:
a polyhydroxy acid and a zinc salt of its conjugate base, wherein the polyhydroxy acid is selected from lactobionic acid, gluconolactone (gluconic acid), a combination of lactobionic acid and gluconolactone (gluconic acid), and derivatives thereof,
a partition coefficient enhancer selected from propylene glycol, butylene glycol, pentylene glycol, hexylene glycol, 1,5 pentane diol, propylene carbonate, dipropylene glycol, hexylene glycol, a glycol ether, diethylene glycol monoethyl ether, a pyrrolidone, N-methyl pyrrolidone and a combination thereof,
a diffusion coefficient enhancer which is selected from a C12 to C14 straight chain fatty acid or a C14 straight chain primary alcohol,
and wherein the composition has a pH in the range of 2.7 to 5.0.

In a second aspect the present invention provides a composition as described above which further comprises at least one ceramide. The composition can also comprise a cholesterol and at least one fatty acid. The ceramide, the cholesterol, and the at least one fatty acid may be in an approximate ratio of 3:1:1.

In a third aspect the present invention relates to treating, including preventing, conditions characterised by a defective external body surface, generally a defective skin barrier, and for promoting repair of the skin barrier. Conditions characterised by a defective skin barrier, and conditions requiring promotion of skin barrier repair, include conditions selected from eczema, atopic eczema, dermatitis, atopic dermatitis, non-atopic dermatitis, non-atopic eczema, seborrheic eczema, irritant contact dermatitis, allergic contact dermatitis, asteatotic eczema, pruritis, dry skin, sensitive skin, acne, acne scars, dryness of skin, nail and hair, xerosis, ichthyosis, palmar and plantar hyperkeratosis uneven and rough surface of skin, nail and hair, dandruff, Darier's disease, lichen simplex chronicus, keratosis, pseudofolliculitis barbae, psoriasis, warts, herpes, age spots, lentigines, melasmas, blemished skin, mottled skin, hyperkeratosis, hyperpigmented skin, stretch marks, thinning of nail plate and hair fragility and splitting of nail and hair, wound healing and treatment of skin wounds, general care as well as treatment and prevention of diseases and conditions oral, gum and vaginal mucosa, promoting healing of burns, promoting healing of abraded skin or any condition where skin has been damaged. The present invention also relates to improving the appearance of skin and/or for preventing aging of the skin.

The composition of the present invention is for topical administration to an external surface of the body. An external body surface includes skin, including mucosa, hair and nails. Generally the external surface of the body is skin.

FIGURES

FIG. 2 shows change in skin surface pH following a single application of the test cream compared to a no treatment control in a participant with healthy skin.

FIG. 3 shows the change in skin surface pH following a single application of the test cream compared to Diprobase cream, Balneum cream and a no treatment control (NTC) in a participant with healthy skin.

Figure 5:
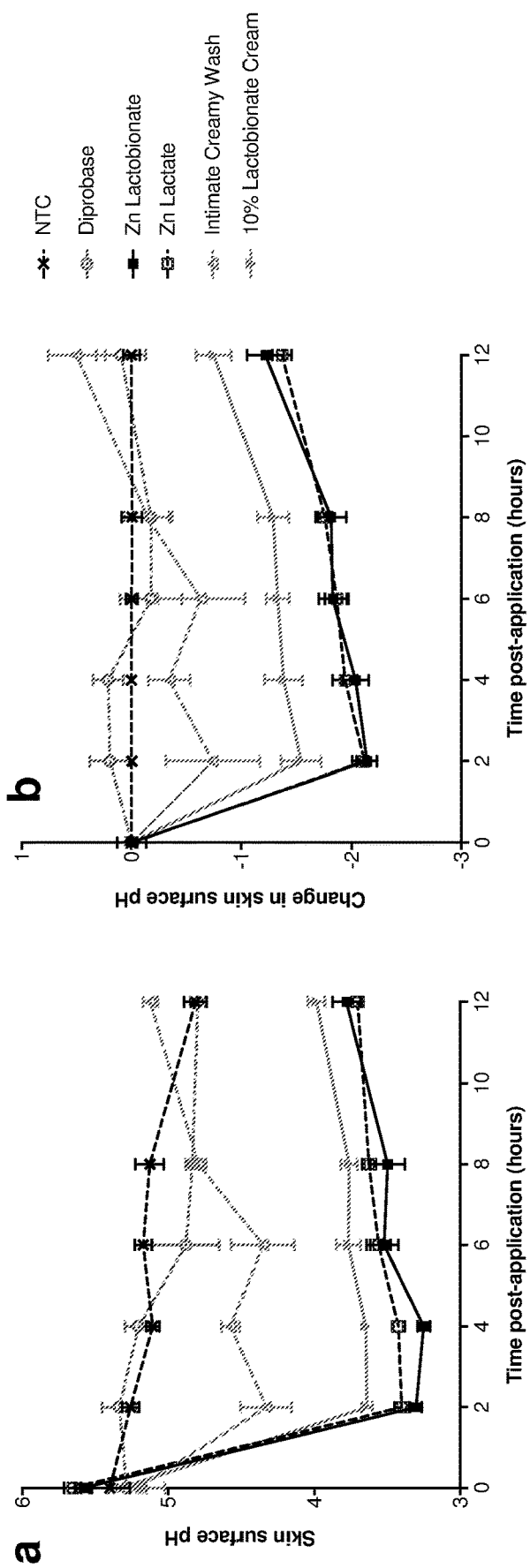

FIG. 5 illustrates the effects of a single application of the creams studied on skin surface pH over 12 hours. FIG. 5 shows the change in skin surface pH following a single application of 5% Zinc lactobionate test cream and 5% Zinc Lactate test cream compared to Diprobase cream, Intimate Creamy Wash, 10% Lactobionate cream and a no treatment control (NTC) in 2 participants with healthy skin. Panel a displays raw data and panel b displays baseline adjusted data.

Figure 6:
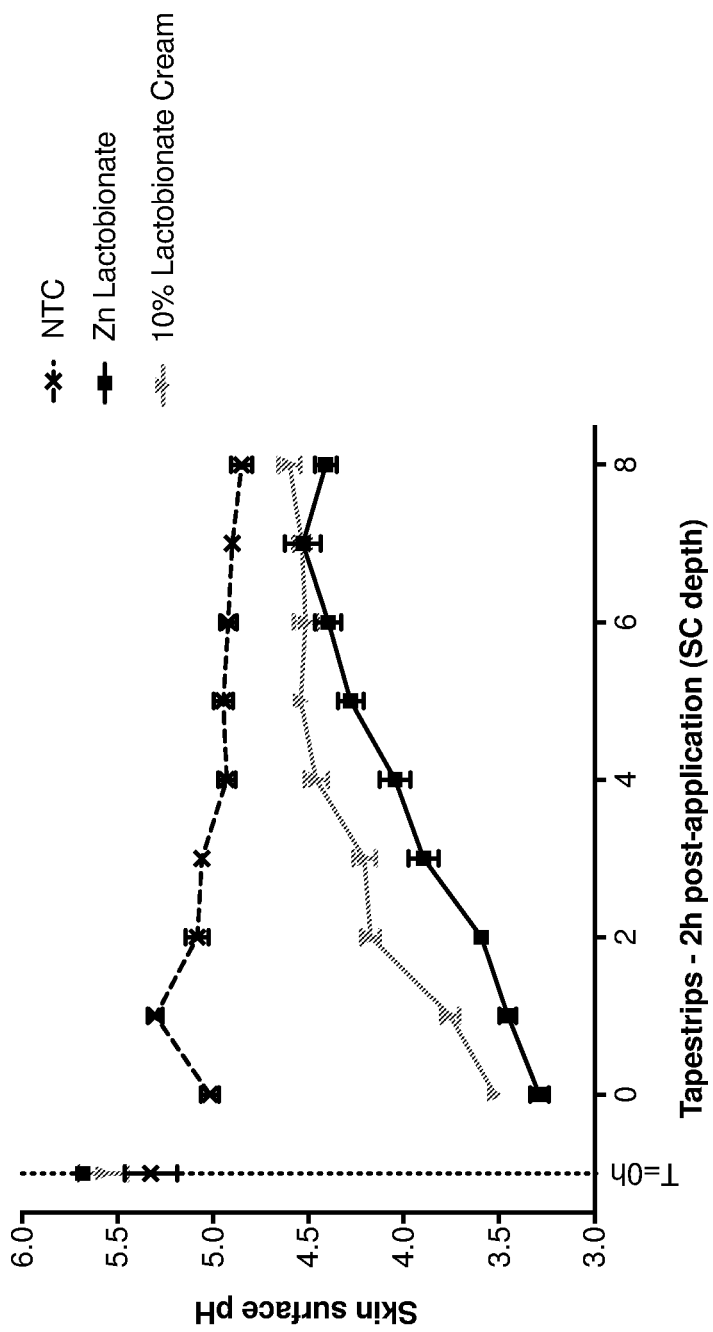

FIG. 6 shows the change in skin pH throughout the stratum corneum (SC) 2 hours following a single application of 5% Zinc Lactobionate test cream compared to the marketed 10% Lactobionate cream and a no treatment control (NTC) in 2 participants with healthy skin.

Figure 7:
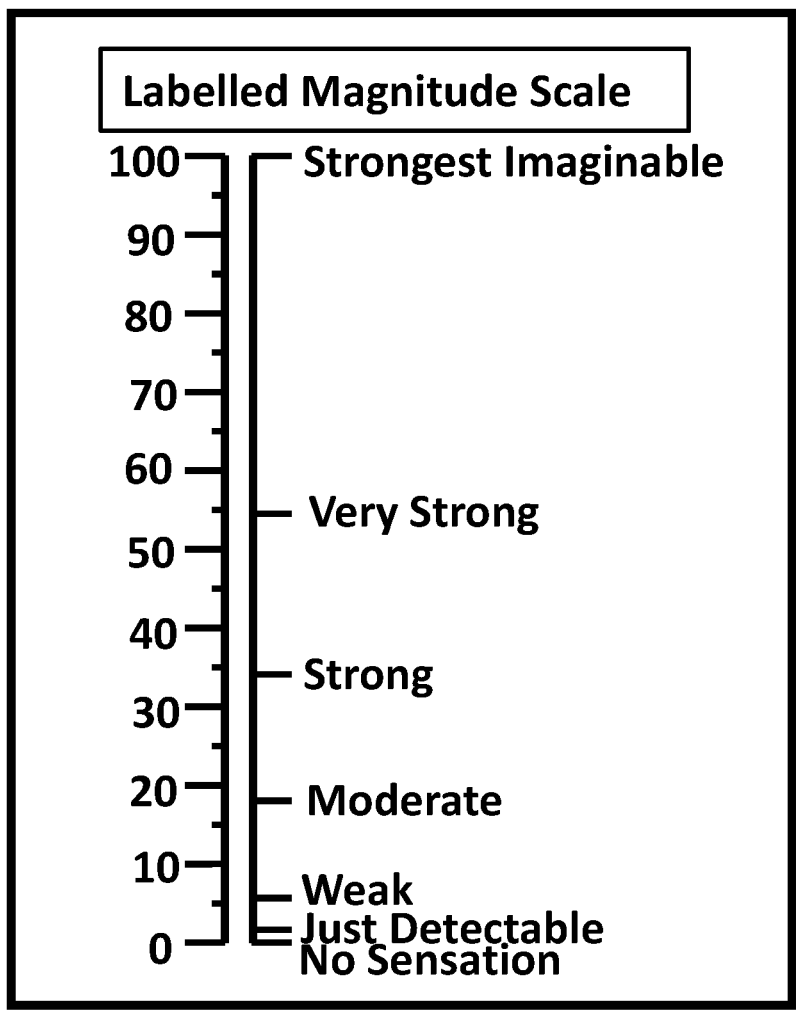

FIG. 7 shows a Labelled Magnitude Scale used for recording negative sensations in Example 4.

Figure 8:
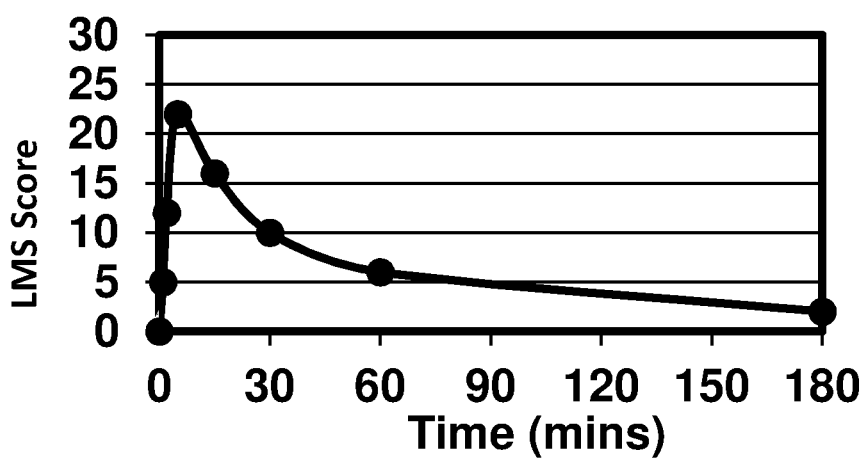

FIG. 8 shows a perceived pain sensation graph for application of a zinc lactate 5% cream with pH 3.2.

Figure 9:
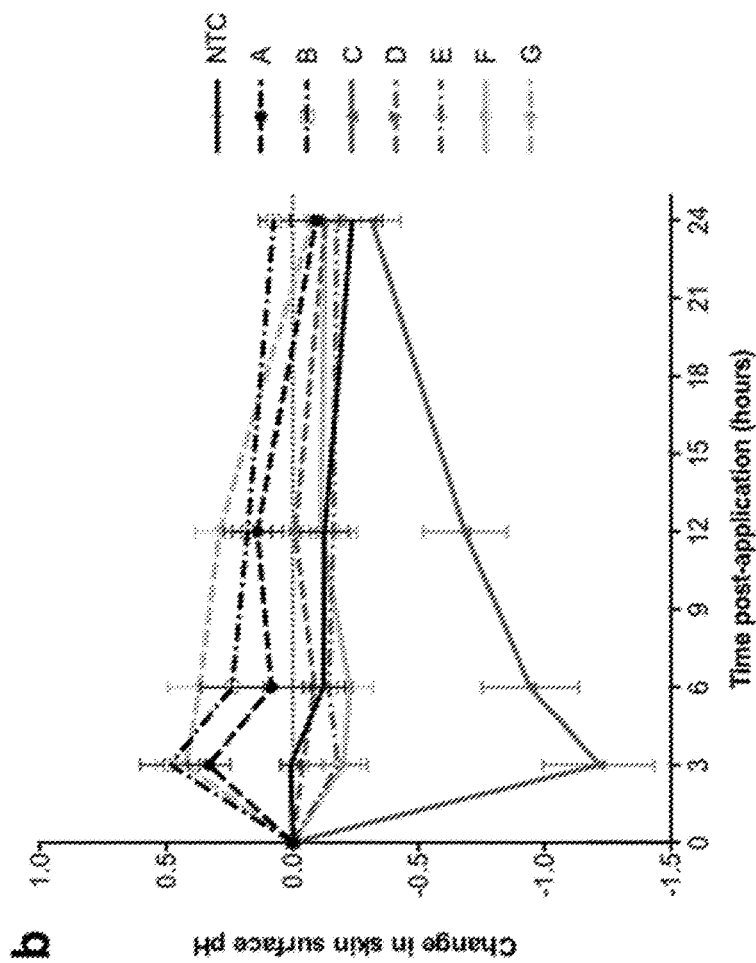
Figure 9:
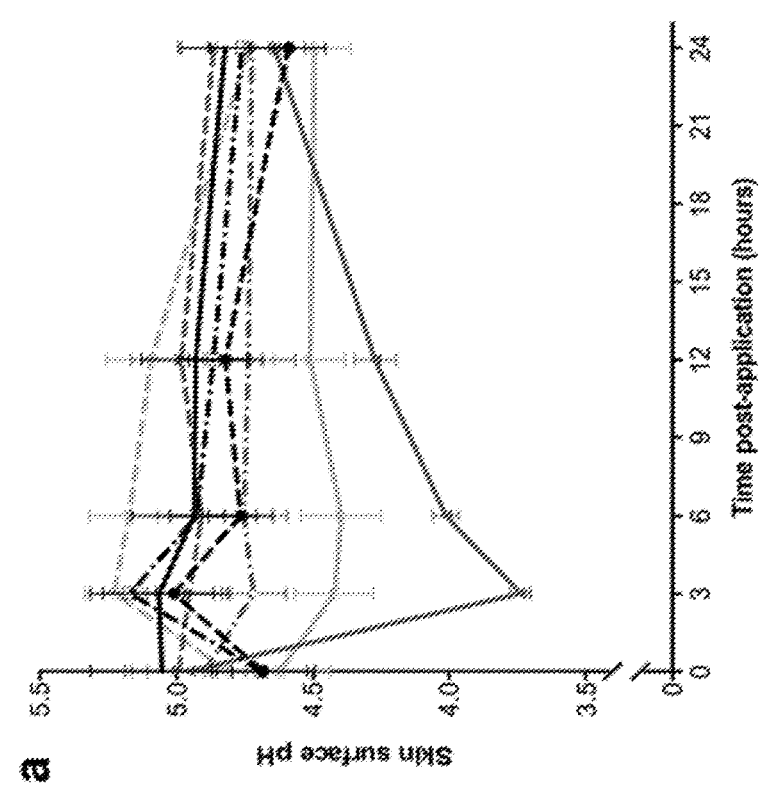

FIG. 9 shows the average (a) skin surface pH and (b) change in skin surface pH, over 24 hours following a single application of test creams A-G compared to a no treatment control (NTC) in 10.

Figure 10:
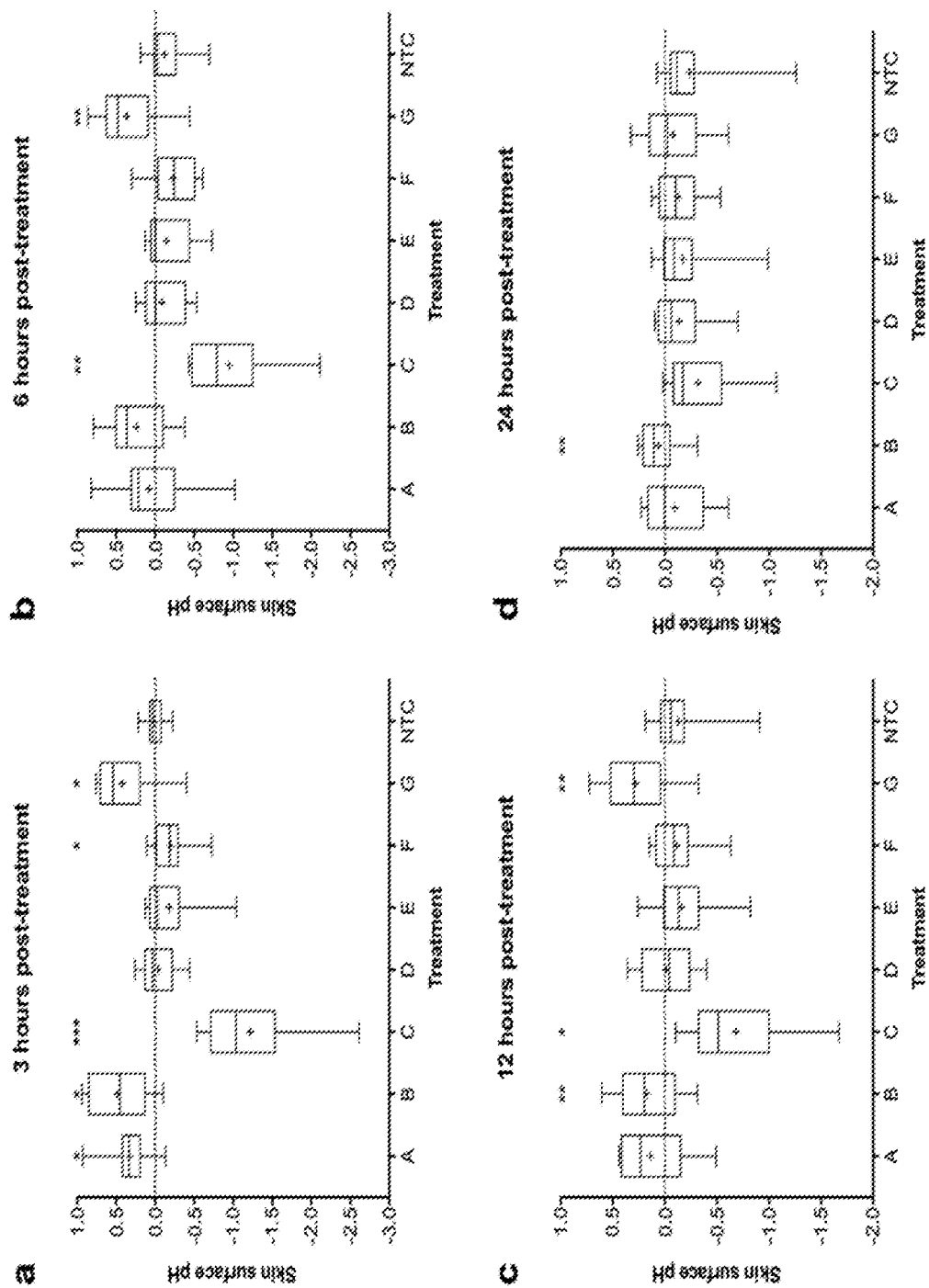

FIG. 10 shows the average skin surface pH following a single application of test creams A-G compared to a no treatment control (NTC), at (a) 3 hours, (b) 6 hours, (c) 12 hours, and (d) 24 hours post-treatment.

Figure 11:
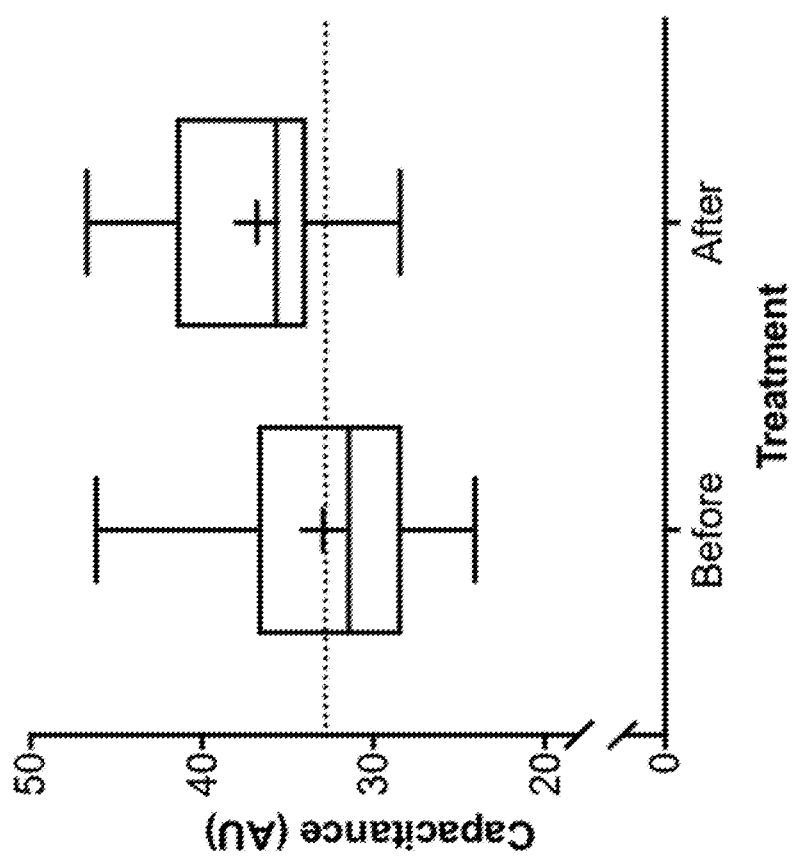

FIG. 11 shows the average capacitance (measured in arbitrary capacitance units) before and 3 hours after a single application of the test cream.

DESCRIPTION

The stratum corneum is the outermost layer of the epidermis and consists of approximately 15 to 20 layers of corneocytes which are flattened cells with no nuclei or cell organelles. Corneocytes are held together by a class of proteins called corneodesmosomes and are embedded in a lipid matrix composed of ceramides, cholesterol and fatty acids.

Desquamation is the process of cell shedding from the outer surface of the stratum corneum and, in healthy skin, this process is balanced by proliferating keratinocytes that form in the stratum basale deeper in the epidermis. These cells migrate through the epidermis towards the outermost surface of the skin in a journey that takes approximately fourteen days.

The stratum corneum functions to form a barrier to protect underlying tissue from infection, dehydration, chemicals and mechanical stress. Maintaining and improving the integrity of the skin barrier is important in the treatment and prevention of skin conditions such as eczema and dermatitis, which arise as a result of the breakdown of the stratum corneum.

Corneocytes are shed from the surface of the skin by a process of proteolysis which is mediated by skin specific proteases, such as the stratum corneum chymotryptic enzyme (SCCE). These proteases are inhibited by skin specific protease inhibitors, such as the secretory leucocyte protease inhibitor (SLPI). It is essential for the process of desquamation and breakdown to be tightly regulated in order to prevent premature desquamation and a breakdown of the skin barrier. A breakdown or thinning of the stratum corneum will permit the penetration of irritants and allergens, which in turn can lead to flare ups of eczema and dermatitis.

The integrity of the stratum corneum barrier is maintained by a balance between the levels and activity of skin proteases and the protease inhibitors and the vulnerability of the adhesion proteins, such as corneodesmosin in corneodesmosomes, to the action of the proteases. The situation is complex since there is a number of the skin specific adhesion proteins, proteases and protease inhibitors.

In normal skin the breakdown of cellular adhesion proteins in corneodesmosomes during desquamation is regulated by balanced expression and function of the skin specific proteases and the skin specific protease inhibitors.

Increasing the pH of the skin away from its healthy range (discussed below) affects the activities of skin specific proteases and skin specific protease inhibitors and can upset the balance of desquamation.

Individuals genetically predisposed to conditions involving a defective skin barrier, for example eczema or dermatitis, have an increased expression of skin specific proteases and/or a decreased expression of skin specific protease inhibitors. This leads to a premature breakdown and thinning of the epidermal barrier, allowing the penetration of irritants and allergens.

Environmental agents also play a role in eczema and dermatitis. House dust mites and bacteria such as *Staphylococcus aureus* produce proteases that can break down the skin barrier from the outside.

It has also been found that washing with soaps and detergents can increase the skin's pH and also upset the balance of desquamation, as would be anticipated from the effect of pH on protease activity.

The present inventors have analysed skin surface pH and the link to conditions involving a defective skin barrier. Despite the widely held view that skin surface pH is 5.5 (which has been influenced by prominent advertising campaigns) skin surface pH actually falls within a range from 4.0 to 6.0. The present inventors have previously determined skin surface pH at a range of anatomical locations in a cohort of 20 healthy individuals. The median pH for the wrist was 4.40, whereas the median pH for the forearm was 4.66. Patients with atopic dermatitis (AD) and other conditions associated with a defective skin barrier exhibit elevated skin surface pH, which plays a role in the pathogenesis of the condition. The inventors previously compared skin surface pH on the forearm between healthy individuals and patients with AD (20 healthy, 20 mild, 26 moderate and 10 severe AD). On the forearm, healthy skin exhibits a pH of approximately 4.79±0.07, which increases to 5.23±0.08 in patients with severe AD. Skin surface pH has a profound effect on stratum corneum protease activity. An increase of only 0.5 pH units is associated with a doubling of chymotrypsin-like protease activity. Elevated protease activity is a key mechanism for skin barrier breakdown in AD. Stratum corneum pH affects the activity of skin specific proteases and certain stratum corneum lipid processing enzymes. Skin surface and stratum corneum pH are increased in conditions such as eczema, dry skin, ichthyosis and associated skin barrier conditions and reduction in pH restores the barrier and restores the normal skin condition. Based upon these findings the target skin surface pH for normalization of protease activity within AD patients is at least ≤5.0 and more preferably 4.5.

Dry skin/kerosis and eczema and dermatitis (atopic and non-atopic) is associated with increased skin pH and hence is amenable to treatments that lower/normalise skin pH (Danby (2016) *Curr. Probl. Dermatol.* Vol. 49, pp 47-60). Seborrheic eczema is also associated with increased skin surface pH (Beare et al. (1958) *Dermatology*, Vol. 70). Sensitive skin, irritant contact dermatitis, and allergic contact dermatitis lead to eczematous changes facilitated by a defective skin barrier; lowering pH improves the skin's natural barrier function, which reduces irritant access to the skin (Schmid-Wendtner and Korting (2006) *Skin Pharmacol. Physiol.*, 19(6):296-302). Pruritis/itch is a symptom of dry skin, sensitive skin. eczema, and dermatitis, as well as other skin conditions.

Low pH can also predispose individuals to acne occurrence and/or recurrences (Prakash et al. (2017) *J. Clin. Aesthet. Dermatol,* 10(7):33-39). In addition, acne is characterised by *P. acnes* being trapped at the base of sebaceous follicles. A key factor that limits the effectiveness of antibacterial agents in treating acne lesions is the relative inaccessibility of these bacteria. Hence, a formulation with enhanced delivery to the skin would be useful in treating acne.

Any dermatological condition present with an impaired barrier function and/or disrupted acid mantle is amenable to treatment by lowering skin surface pH.

Therefore the composition of the present invention has a low pH and is designed to reduce skin pH on topical administration. The pH reduction achievable with the composition of the present invention is a sustained reduction of skin surface pH for up to 12 hours as demonstrated in Example 3 and FIGS. 2, 3, 5, and in Example 7 and FIGS. 9 and 10.

Additionally, the pH reduction is not merely at the skin surface but is driven across the skin, deeper into the stratum corneum. These effects are demonstrated in Example 3 and in FIGS. 4 and 6 below.

The reduction of pH of the skin and in the stratum corneum affects the action of skin specific proteases and of skin specific protease inhibitors which in turn reduces desquamation helping to maintain the integrity of the stratum corneum and restore skin barrier function.

The acidic pH of the composition of the present invention has an antibacterial and antimicrobial effect. This is beneficial in conditions involving a defective skin barrier.

Furthermore, the composition of the present invention comprises zinc ions ($Zn^{2+}$). Zinc ions also provide an antimicrobial and antibacterial effect which is beneficial in conditions involving a defective skin barrier.

The composition of the present invention benefits from attributes which will improve patient compliance. Application of the composition to an external body surface such as skin does not cause irritation nor does it cause a stinging sensation as demonstrated in Example 4. The composition of the present invention was noted to be pleasant to use as demonstrated in Example 6.

Hydroxy acids, both alpha hydroxy acids such as lactic and glycolic acids, and beta hydroxy acids, such as salicylic acid, have been widely used to restore the appearance and condition of normal skin via effects on the epidermis and dermis. Depending upon the concentration of the acid and the pH of the formulation, these acids decrease skin surface and stratum corneum pH to influence the biological mechanism described above. At higher concentrations they may be used as chemical peels to induce a controlled injury to the skin to promote tissue regrowth. However, in many subjects, even at low concentrations, and also depending upon product pH, topical treatment with alpha hydroxy acids results in irritation or stinging or a local intolerance that limits adherence to treatment regimen and thus limits any benefits.

More recently the use of polyhydroxy acids such as lactobionic acid has been described to improve the appearance of skin and treat a number of skin conditions. See for example, U.S. Pat. Nos. 5,547,988 and 6,335,023. Polyhydroxy acids such as lactobionic acid and gluconolactone were described as being effective to improve a range of skin conditions and without the potential for local intolerance as seen with alpha hydroxy acids.

In general, improved specificity, selectivity of action for a wanted efficacious rather than an unwanted adverse effect, may be intrinsic to the molecular structure of an active agent or may be due to control of dose delivered from the formulation. For example, controlled topical microsponge delivery of retinoids, benzyl peroxide and lactic acid are available commercially with claims of improved local tolerance. However, such controlled delivery systems, are associated with reduced efficacy due to the closeness of the efficacy and adverse effects dose response curves.

Lactobionic acid is a substantially larger molecule than lactic acid or glycolic acid. Molecular size, and lipid solubility, are closely correlated with skin penetration and thus the improved local tolerance of polyhydroxy acids such as lactobionic acid may be due to the effect of molecular size to control and reduce skin penetration. Consistent with this, for example; as seen with microsponge delivery systems, there is evidence that lactobionic acid may have reduced potency in treatment of skin conditions than the older hydroxy acids. The reduced potency and reduced local irritation of previously described skin care formulations including lactobionic acid, in comparison with lactic acid containing skin care formulations is understood to be due to reduced delivery and skin penetration of the lactobionic acid. Despite this, and most probably driven by its excellent local tolerance, especially following application to sensitive skin conditions and skin sites, lactobionic acid is widely used by consumers and is the dominant active in the cosmeceutical market.

The present inventors have proposed that, by applying advanced topical drug delivery technology to lactobionic acid, several important design objectives might be met:
  that topical delivery regimens of lactobionic acid may be feasible, whereby:
    skin surface pH may be controlled to be less than pH 4.5, and optionally in the region of pH 3.0-4.0
    that pH within the lower stratum corneum may be controlled to be in the range of pH 4.0-5.0 thus to optimise control of barrier restorative biological mechanisms
    these controls are effective for 12 hours after application of a single dose thus to allow twice a day application to improve adherence Such topical delivery regimens of lactobionic acid may be expected to result in very efficient restoration of skin barrier function and skin condition and appearance. As discussed previously, and depending upon the mechanism of selectivity of lactobionic acid, this may be associated with increase in local adverse effects or not. We have found that these regimens are very efficient to restore skin barrier function and skin condition and appearance, but are not associated with any increase in local adverse effects.

The composition of the present invention may be an emulsion composition stabilised by surfactant. The composition can comprise an aqueous-glycol phase and an oil phase.

The composition of the present invention is formulated to be suitable for topical administration to an external body surface. An external body surface includes skin, mucosa, hair and nails. It is envisaged that the composition will be applied to skin.

Active ingredients in the composition are a polyhydroxy acid and a zinc salt of its conjugate base. The active ingredients may be in the aqueous-glycol phase of the composition. The polyhydroxy acid may be selected from lactobionic acid, gluconolactone/gluconic acid or a combination of lactobionic acid and gluconolactone/gluconic acid and derivatives thereof.

Derivatives of a polyhydroxy acid can be salts thereof, for example zinc, calcium, potassium, sodium, magnesium, or iron salts thereof. Derivatives of a polyhydroxy acid can be esters thereof. Valuable properties of the composition of the present invention are tested and demonstrated in the Examples below. A derivative of lactobionic acid or gluconolactone/gluconic acid includes a molecule that if it were formulated as a 5% cream according to the present invention and applied to healthy skin would cause a sustained reduction in skin surface pH without stinging sensation. A derivative of lactobionic acid or gluconolactone/gluconic acid includes a molecule that if it were formulated as a 5% cream according to the present invention, and optionally according to table 2.2.1 or 2.2.2 below, and applied to healthy skin, optionally as a single application, and preferably about 100 µl applied to an area of about 20 $cm^2$, would cause a reduction in skin surface pH of at least 0.5, 0.7, 1.0 or 1.2 pH units for at least 3, 6, 9 or 12 hours in the absence of perceived pain or irritation, optionally scored using the Labelled Magnitude Scale (LMS).

In embodiments the polyhydroxy acid is lactobionic acid and the zinc salt of its conjugate base is zinc lactobionate. The composition comprises a mixture of zinc lactobionate and lactobionic acid. In embodiments the composition comprises a mixture of zinc lactobionate and lactobionic acid in approximately a ratio of 1:4.

Zinc oxide is generally used as the ingredient from which the zinc salt is formed. It is noted, however, that other zinc containing compounds might be used as the starting ingredient. It is also noted that other metal ions such as copper might be used in a composition of the present invention.

In embodiments the composition of the present invention does not comprise or use as an ingredient zinc pyrithione which has been used in anti-dandruff shampoos. This is because the composition of the present invention is advantageously for topical administration to the skin.

The amount of zinc oxide used in manufacturing the composition may be greater than 0.05% w/w. Zinc oxide ingredient may be used in an amount from 0.05-0.5% w/w, 0.05-0.2% w/w and preferably about 0.1% w/w.

The composition of the present invention may comprise 2.0-10.0% w/w (percent weight by weight) of the composition of the polyhydroxy acid and the zinc salt of its conjugate base.

Quantities expressed herein as % w/w of the composition refer to the total composition.

The composition of the present invention may comprise the polyhydroxy acid and the zinc salt of its conjugate base at greater than or equal to 2.5, 3.0, 3.5, 4.0, 4.5 or 5.0% w/w of the composition. The composition of the present invention may comprise the polyhydroxy acid and the zinc salt of its conjugate base at less than or equal to 9.5, 9.0, 8.5, 8.0 or 7.5% w/w of the composition. The amount of the polyhydroxy acid in the composition of the present invention may be from 3.0 to 6.5, or from 3.5 to 6.0, or from 4.0 to 5.5 or is about 5% w/w of the composition.

The composition of the present invention can comprise water, and the composition can comprise from 30-45 or 35-40% w/w water. In embodiments a salt is dissolved in the water in the composition of the present invention. The salt may comprise a group 1 metal anion, such as a sodium. The salt may comprise a halogen cation, such as chloride. The salt may be sodium chloride. The salt may be present at 0.1-3 or 0.5-2.0% in the water of the aqueous-glycol phase. In embodiments 1% sodium chloride de-ionised water is used.

The composition of the present invention comprises a partition coefficient enhancer. The partition coefficient enhancer may be in the aqueous-glycol phase of the composition. The partition coefficient enhancer may be selected from propylene glycol, butylene glycol, pentylene glycol, hexylene glycol, 1,5 pentane diol, propylene carbonate, dipropylene glycol, hexylene glycol, glycol ethers such as diethylene glycol monoethyl ether (Transcutol™) and pyrrolidones such as N-methyl pyrrolidone and a combination thereof. In embodiments the partition coefficient enhancer is propylene glycol. The partition coefficient enhancer may be 15-30, 15-25, 17-23, 18-22, or about 20% w/w of the composition.

The composition of the present invention may also comprise one or more emollients which may be in the oil phase of the composition. The one or more emollient may be 10-30% w/w of the composition. The emollient is a high molecular weight hydrocarbon, optionally selected from mineral oil, petrolatum, paraffin, and mixtures thereof. The emollient may be selected from hydrogenated polydecene, hydrogenated didecene, hydrogenated polyisobutene and mixtures thereof. In embodiments the emollient is hydrogenated polydecene. The composition of the present invention can comprise from 10.0-30.0, 10.0 to 25.0, 10.0 to 20.0, from 12.0 to 16.0 or about 14% w/w of an emollient.

The composition of the present invention comprises a diffusion coefficient enhancer which is selected from a C12 to C14 straight chain fatty acid or a C14 straight chain primary alcohol. The diffusion coefficient enhancer may be in the oil phase of the composition. The diffusion coefficient enhancer may be 1-tetradecanol or myrystic acid. In embodiments the diffusion coefficient enhancer is 1-tetradecanol. The diffusion coeeficient enhancer can be 1.0-2.0 or 1.2-1.8 or about 1.5% w/w of the composition. The diffusion coefficient enhancer is generally at saturation or at about saturation.

The composition of the present invention has a low or an acidic pH. The composition of the present invention has a pH in the range of 2.7-5.0. The composition may have a pH in the range of 3.0 to 4.5, or in the range of 3.0 to 4.0, or in the range of 3.0 to 3.5, or about 3.2. The composition of the present invention may comprise a further acid to modulate the pH of the composition. A further acid can be used to adjust formulation pH is citric acid.

The composition of the present invention may also comprise one or more surfactants. The composition may comprise 3.0-12.0, 4.0-12.0, 6.0-10.0, 8.0-9.0, or about 8.5% w/w of surfactant. The composition may comprise a primary surfactant or a primary surfactant system. A primary surfactant system may comprise methyl glucose sesquistearate (Glucate SS) and PEG-20 methyl glucose sesquistearate (Glucamate SSE-20). An alternative primary surfactant system can be glycerol stearate and PEG-100. The composition may comprise 2.0-5.5%, 2.5-5.0% or from about 2.84-about 4.73% of a primary surfactant system. The composition may further comprise a co-surfactant or a secondary surfactant. The co-surfactant can be a C16 to C22 alcohol. The composition may comprise 2.0-5.5%, 2.5-5.0% or from about 2.61-about 4.35% of a co-surfactant. The surfactants stabilise the viscosity or the interface of the aqueous-glycol and oil phases.

The composition of the present invention may comprise a skin barrier restoration system. The composition may comprising one or more of a ceramide, a cholesterol and a fatty acid. In embodiments the composition comprises a ceramide, a cholesterol and a fatty acid in the ratio of approximately 3:1:1. In embodiments the fatty acid may be linoleic acid.

The composition of the present invention may further comprise one or more of a stabilizer, a preservative, a salt or a buffer. The aqueous-glycol phase may comprise a stabilizer. Stabilizers include a xanthan gum or a crystal growth inhibitor.

In embodiments, a composition of the present invention is for topical administration to an external body surface, and comprises
  an aqueous-glycol phase comprising:
    4.0-6.0% w/w of a polyhydroxy acid and a zinc salt of its conjugate base, wherein the polyhydroxy acid is selected from lactobionic acid, gluconolactone (gluconic acid), a combination of lactobionic acid and gluconolactone (gluconic acid), and derivatives thereof,
    18.0-22.0% w/w of a partition coefficient enhancer selected from propylene glycol, butylene glycol, pentylene glycol, hexylene glycol, 1,5 pentane diol, propylene carbonate, dipropylene glycol, hexylene glycol, a glycol ether, diethylene glycol monoethyl ether, a pyrrolidone, N-methyl pyrrolidone and a combination thereof, and
    water,
  and an oil phase comprising:
    1.0-2.0% w/w of a diffusion coefficient enhancer which is a C12 to C14 straight chain fatty acid or a C14 straight chain primary alcohol,
    emollient, and
    surfactant,
wherein % w/w is of the composition, and wherein the composition has a pH in the range of 3.0 to 3.5. The polyhydroxy acid and a zinc salt of its conjugate base may be lactobionic acid and zinc lactobionate. The partition coefficient enhancer may be propylene glycol. The diffusion coefficient enhancer may be 1-tetradecanol.

The composition of the present invention may further comprise one or more of polyol humectants, for example glycerol (and its triester), sorbitol, xylitol, maltitol and the like and polymeric derivatives thereof.

The composition of the present invention can be for use in therapy. The composition of the present invention can be for use in a method of treating or preventing a condition caused by a defective skin barrier or for promoting skin barrier repair.

The composition of the present invention can be for use in a method of treating or preventing a condition caused by abnormally elevated skin pH. The composition of the present invention can be for use in a method of decreasing skin pH.

The composition of the present invention can cause a reduction in skin surface pH. The reduction in skin surface pH can be by at least 0.5 pH units, at least 0.7 pH units, at least 1.0 pH units, or at least 1.2 pH units. The reduction in skin surface pH can be for at least 3 hours, at least 6 hours, or at least 12 hours. The pH reduction achievable may be after a single application of the composition of the present invention. An application can be about 80 µl to 125 µl, or about 100 µl of composition applied to a 4 cm×5 cm area of skin. A test method is set out in Example 7 herein.

Therefore, the composition of the present invention, if applied in a single application at about 100 µl per 20 cm² area of skin, achieves a reduction in skin surface pH of at least 0.5 pH units for at least 3 hours. The composition of the present invention, if applied in a single application at about 100 µl per 20 cm² area of skin, achieves a reduction in skin surface pH of at least 0.7 or 1.0 or 1.2 pH units for at least 6 or 9 or 12 hours. A single application of the composition of the present invention, if applied at about 100 µl per 20 cm² area of skin, can result in skin surface pHG being maintained below pH 4.5 for 12 hours or more.

The reduction in skin surface pH which can be achieved by the composition of the present invention is in the absence of sign of skin irritation and/or redness.

A pharmaceutical formulation can comprise a composition of the present invention. In embodiments a pharmaceutical formulation comprising a composition of the present invention is to treat a conditions caused by a defective skin barrier or for promoting skin barrier repair.

Embodiments embrace use of a composition of the present invention in the manufacture of a medicament for the treatment of a condition caused by a defective skin barrier or for promoting skin barrier repair.

The present invention also embraces a method treating or preventing a condition caused by a defective skin barrier or for promoting skin barrier repair, the method comprising topical application of a composition of the present invention to an external body surface of a subject that is affected by or is at risk of being affected by said condition or which is in need of skin barrier repair.

As described herein a condition caused by a defective skin barrier or a condition in which promotion of skin barrier repair is required is a condition selected from the group consisting of eczema, atopic eczema, dermatitis, atopic dermatitis, non-atopic dermatitis, non-atopic eczema, seborrheic eczema, irritant contact dermatitis, allergic contact dermatitis, asteatotic eczema, pruritis, dry skin, sensitive skin, acne, acne scars, dryness of skin, nail and hair, xerosis, ichthyosis, palmar and plantar hyperkeratosis uneven and rough surface of skin, nail and hair, dandruff, Darier's disease, lichen simplex chronicus, keratosis, pseudofolliculitis barbae, psoriasis, warts, herpes, age spots, lentigines, melasmas, blemished skin, mottled skin, hyperkeratosis, hyperpigmented skin, stretch marks, thinning of nail plate and hair fragility and splitting of nail and hair, wound healing and treatment of skin wounds, general care as well as treatment and prevention of diseases and conditions oral, gum and vaginal mucosa, promoting healing of burns, and promoting healing of abraded skin and any condition where skin has been damaged.

In embodiments a condition caused by a defective skin barrier or a condition in which promotion of skin barrier repair is required is a condition selected from the group consisting of eczema, atopic eczema, dermatitis, atopic dermatitis, non-atopic eczema, non-atopic dermatitis, seborrheic eczema, irritant contact dermatitis, allergic contact dermatitis, asteatotic eczema, pruritis, acne, dry skin and sensitive skin.

The composition of the present invention may also be used to improve the appearance of skin and/or for preventing aging of skin.

The present invention also embraces a method of reducing skin surface pH, by at least 0.5, 0.7, 1.0, or 1.2 pH units for at least 3 or more, 6 or more, 9 or more, or 12 or more hours by application of the composition of the present invention too the skin. The application of the composition can be a topical application to the skin. The application can be a single application of the composition of the present invention. The single application can be about 80-125 µl, preferably about 100 µl, to about 20 cm² (for example 4 cm×5 cm) area of the skin. The reduction in skin surface pH can be measured with a commercially available pH meter suitable for skin surface pH assessment.

The present invention embraces the composition of the present invention for use in a method of reducing skin surface pH by at least 0.5, 0.7, 1.0, or 1.2 pH units for at least 3, 6, 9, Or 12 hours and thereby treating or preventing a condition selected from the group consisting of eczema, atopic eczema, dermatitis, atopic dermatitis, non-atopic eczema, non-atopic dermatitis, seborrheic eczema, irritant contact dermatitis, allergic contact dermatitis, asteatotic eczema, pruritis, acne, dry skin and sensitive skin.

The present invention embraces a method comprising topical application of the composition of the present invention to achieve a reduction in skin surface pH by at least 0.5, 0.7, 1.0, or 1.2 pH units for at least 3, 6, 9, or 12 hours and thereby treat or prevent acne, dry skin, or sensitive skin.

The composition described herein is designed to require topical application to skin or to an affected external body surface three times a day, fewer than three times a day or about twice a day.

The combination of ingredients described herein provide the benefits of the skin barrier cream of the present invention which include a sustained (up to 12 hours) reduction of skin pH relative to no treatment, that pH reduction is driven across the depth of the stratum corneum, non-irritancy upon application despite the pH of the cream being low, for example as low as 3-3.4, the composition is stable, the composition is readily adsorbed and so nice to use, the composition provides inhibition of protease enzymes and provides an antibacterial effect.

Design Features of Skin Barrier Composition

The skin barrier composition has a low pH, in the range of 2.7-5.0, optionally 3.0-3.5 and for example pH 3.2. A low pH is obtained by use of a polyhydroxic acid and a zinc salt of its conjugate base, for example a zinc lactobionate-lactobionic acid buffer, contained within the aqueous-glycol solution continuous phase of the cream. In embodiments the pH may be buffered by inclusion of another acid.

pH Reduction is Driven Across the Depth of the Stratum Corneum

The reduction of pH deeper in the stratum corneum, such that the efficiency of lipid processing enzymes may be optimized, is achieved by delivery of a polyhydroxy acid, for example lactobionic acid. Said polyhydroxy acid, for example said lactobionic acid, from the surface of the stratum corneum is delivered deeper into the stratum corneum by a Fickian process of molecular diffusion. Three factors, which may be effected by a topical formulation, control this diffusional process:
  the thermodynamic activity of the molecule, otherwise expressed as its degree of saturation in the skin surface film
  the solubility of the molecule in the stratum corneum
  the diffusivity of the molecule through the stratum corneum In the cream as formulated, the polyhydroxy acid and the zinc salt of its conjugate base, for example the zinc lactobionate-lactobionic acid buffer, is in solution within the aqueous-glycol solution continuous phase of the cream. Following application to the skin surface as a thin film, the volatile solvent water is lost and the polyhydroxy acid and a zinc salt of its conjugate base, for example the zinc lactobionate-lactobionic acid buffer, becomes supersaturated, thus to increase its thermodynamic activity and diffusion.

Immediately upon application as a thin film, the partition coefficient enhancer, for example the glycol, for example the propylene glycol, partitions into the stratum corneum to increase the solubility of the polyhydroxy acid and the zinc salt of its conjugate base, for example the zinc lactobionate-lactobionic acid buffer in the stratum corneum. The partition coefficient enhancer, for example the propylene glycol, also increases the solubility of the diffusion coefficient enhancer, for example the tetradecanol, in the stratum corneum.

Because of its chemistry, the diffusion coefficient enhancer, for example tetradecanol, is distributed within the formulation between the aqueous glycol and oil phase of the formulation. The concentration of the diffusion coefficient enhancer, for example the tetradecanol, is such that it is approximately at saturation. Facilitated by the partition coefficient enhancer, for example the propylene glycol, the saturated diffusion coefficient enhancer, for example the saturated tetradecanol, partitions into the stratum corneum where it increases the diffusivity of the polyhydroxy acid and the zinc salt of its conjugate base, for example the zinc lactobionate-lactobionic acid buffer, in the stratum corneum.

These three factors work in synergy, typically to increase diffusion into the stratum corneum by 40-60 fold.

Sustained (12 Hours) Reduction of Skin pH Relative to No Treatment

The duration of reduction of pH is controlled by the dose of the polyhydroxy acid and the zinc salt of its conjugate base, for example the zinc lactobionate-lactobionic acid buffer, and by its rate of diffusion into the stratum corneum. The rate of diffusion is controlled solely by the three factors described. Of these, the degree of saturation of the polyhydroxy acid and the zinc salt of its conjugate base, for example the zinc lactobionate-lactobionic acid buffer, and the surface dose of the partition coefficient enhancer, for example the propylene glycol, deplete over 12 hour to define the required dosage regimen.

Non Irritancy Despite the pH of the Cream Being Low, for Example as Low as 3-3.5

Surface and stratum corneum pH in the range of 3-3.5 following application of hydroxyl acids is associated with local intolerance. Without being bound by theory, we hypothesize that the lack of local intolerance seen with lactobionic acid may be due to molecular specificity, thus to reduce pH but not to trigger local irritation. This hypothesis similarly applies to gluconolactone (gluconic acid).

Aesthetics and Experience in Use

These factors drive patient adherence and thus, ultimately, efficacy. In addition to the excipients already described which function to deliver the efficacy benefits, other excipients are desirable to achieve the optimal formulation quality and others to ensure appropriate Aesthetics and Experience in use.

Formulation Quality

These excipients include glucate-glucamate surfactants and polymer excipients which ensure physical stability of the cream and preservatives which ensure microbiological quality. These excipients are selected based on suitability for use on sensitive skin.

Aesthetics

The oil phase is a blend of hydrogenated polydecene and silicone elastomer to ensure a soft silky non-sticky skin feel.

Formulation Physical Stability

The glucate-glucamate surfactants system is chosen for its suitability for use in sensitive skin which is an essential attribute of the formulation. Lactobionic acid interacts with the polar glucamate surfactant to increase it solubility in the aqueous glycol phase thus to destabilize the dispersed oil phase. Addition of sodium chloride is used to "salt out" the glucamate to increase its presence at the oil-aqueous glycol interface.

EXAMPLES

Example 1

The following table provides an indication of a composition according to the present invention and an indication of envisaged ingredients.

| Function | Description | Ingredient | An example by INCI/other name | % w/w range |
|---|---|---|---|---|
| Active | Active | Polyhydroxy acid and a zinc salt of its conjugate base | Lactobionic acid - zinc lactobionate | 2-10% |
| Aqueous-glycol phase | Aqueous phase | water | 1% Sodium chloride (optional) Aqua | To make up to 100% |
| | Glycol phase | Partition coefficient enhancer | Propylene glycol | 15-30% |
| | Aqueous-glycol phase may optionally also comprise one or more of stabiliser, buffering agent or preservative | | | |

-continued

| Function | Description | Ingredient | An example by INCI/other name | % w/w range |
|---|---|---|---|---|
| Oil phase | Emollient Diffusion coefficient enhancer | Emollient Diffusion coefficient enhancer | 1-tetradecanol | 10-30% 1.0-2.0% |
| | Optional barrier restoration system | Ceramide | Hydroxypropyl bispalmitamide MEA | (If present about 0.30) |
| | | Cholesterol | Cholesterol | (If present about 0.10) |
| | | Fatty acid | Linoleic acid | (If present about 0.10) |
| Oil phase | Surfactants | Primary low HLB surfactant | Methyl Glucose Sesquistearate | 2.84-4.73% primary surfactant system |
| | | Primary high HLB surfactant | PEG-20 methyl glucose sesquistearate | 2.61-4.35 |
| | | Co-surfactant | Glyceryl stearate | |
| | | total | | 100 |

Example 2

Manufacturing Compositions of the Present Invention

A. The following exemplary skin barrier repair cream, comprises the ingredients listed below. The provided manufacturing process sets out how to prepare a skin barrier repair cream.

Ingredients Table

| Function | Description | Ingredient | INCI/other name | By process | % w/w | Range critical ingredients |
|---|---|---|---|---|---|---|
| Active | Active | Zinc oxide | Zinc oxide | V1 | 0.10 | 2-10% |
| | | Lactobionic acid | Lactobionic acid | V1 | 4.92 | |
| Aqueous-glycol phase | Aqueous phase | Sodium chloride 1% in de-ionised water | Sodium chloride Aqua | V1 | 38.32 | |
| | Glycol phase | Propylene glycol | Propylene glycol | V2 | 20.00 | 15-30% |
| | Aqueous-glycol phase stabilisers | Carbopol | Polyacrylate-1 Crosspolymer | V1 + V2 | 3.00 | |
| | | Xanthan gum | Xanthan gum | V2 | 0.20 | |
| | | PVP K25 | Polyvinylpyrrolidone K25 | V1 | 1.00 | |
| | Buffering agent | 25% citric A | Citric acid | V1 + V2 | 1.20 | |
| | Preservative | Phenoxyethanol/ ethyl hexylglycerin | Phenoxyethanol Ethylhexylglycerin | V2 | 0.50 | |
| Oil phase | Emollient | ST-Elastomer 10 | Cyclopentasiloxane Domethicone cross polymer | V3 | 6.00 | |
| | | Decene homopolymer | Hydrogenated polydecene | V3 | 14.00 | |
| | Diffusion coefficient enhancer | Myristyl alcohol | Myristyl alcohol (1-tetradecanol) | V3 | 1.50 | 1-2.0% |
| | Barrier restoration system (optional) | Ceramide PC-104 | Hydroxypropyl bispalmitamide MEA | V3 | (0.30) | |
| | | Cholesterol | Cholesterol | V3 | (0.10) | |
| | | Fatty acid | Linoleic acid | V3 | (0.10) | |
| Oil phase | Surfactants | Primary low HLB surfactant | Methyl Glucose Sesquistearate | V3 | 1.26 | primary surfactant system |
| | | Primary high HLB surfactant | PEG-20 methyl glucose sesquistearate | V3 | 2.52 | |
| | | Co-surfactant | Glyceryl stearate | V3 | 3.48 | |
| Oil phase | Aesthetic | Dry Flow Pure | Aluminum Starch Octenylsuccinate | V3 | 2.00 | |
| | | total | | | 100.00 | |

Manufacturing Process

The manufacturing process is that of a typical cream manufacture where a heated "oil phase" is added dropwise to a heated "water phase" under low rotor-stator emulsification. After the addition is completed there is a short period of high shear emulsification (1-2 minutes at 100-200 g scale). Gelation Carbomer and pH adjuster are then added and the system is paddle mixed at 200 rpm, for 1-2 minutes then at 60 rpm until the cream cools to below 30° C. The water phase is compromised of two premixes such that three vessels are used.

At 100-200 g scale V1 is 250-400 ml beaker, V2 is 25-50 ml beaker and V3 is 50-100 mL beaker.

Process 100 g Scale
V1 250 ml beaker: Zn(LBA)2 in situ
Weigh out Zinc oxide
Weigh out Lactobionic acid (to form zinc lactobionate plus free lactobionic acid)
  Weigh out 1% NaCl in DI water
  stir to form Zn salt (gentle heat may be used, but process is rapid)
  Weigh out PVP
  stir to form clear solution
V2 50 ml beaker: Aqueous solvent and gels
Weigh out Propylene glycol
Weigh out Phenoxyethanol/ethylhexylglycerin,
Weigh out Xanthan gum
disperse Xanthan with spatula, then quickly
Add V2 to V1 with stirring
V3 250 ml beaker: Oils and surfactants
Weigh out hydrogenated polydecene
Weigh out Methyl Glucose Sesquistearate
Weigh out PEG-20 methyl glucose sesquistearate
Weight out glyceryl stearate
Weigh out ST-Elastomer-10
Weigh out Dry Flow Pure
Weigh out $C_{14}$ alcohol, 1-tetradecanol
Weigh out Ceramide
Weigh out Cholesterol
Weigh out Linoleic acid
Mix with spatula to disperse solids.

Heat to V1 and V2 to 70° C.-75° C. (at higher temperature the cream does not set during the emulsification process).

Add V3 to (V1+V2) dropwise under low rotor-stator emulsification over 3-6 minutes (100-200 g scale)

Mix on maximum shear with Silverson square hole head for 1-2 minutes (100-200 g scale)

Weigh in Carbomer Aqua CC
Weigh in 25% citric acid pH adjuster
Paddle stir at 200 rpm to disperse, then at 60 rpm until temperature drops to 30° C.

Measure pH, measure viscosity (at +12-24 hour), pack.

B. The following provides another exemplary skin barrier repair cream, comprising the ingredients listed below. The provided manufacturing process sets out how to prepare a skin barrier repair cream.

| Ingredients | CAS Number | Possible Suppliers | % w/w 100 g |
|---|---|---|---|
| Zinc Oxide | 1314-13-2 | GCE Laborarotires | 0.10 |
| Lactobionic Acid | 96-82-2 | Xi An Kerui Biochemical Co., Ltd | 4.92 |
| Sodium Chloride 1% in DI Water | 7440-23-5 | Any - not critical | 39.30 |
| Methyl Glucose Sesquistearate (Glucate SS) | 68936-95-8 | Lubrizol | 1.26 |
| PEG-20 Methyl Glucose Sesquistearate (Glucamate SSE-20) | 68389-70-8 | Lubrizol | 2.52 |
| Myristyl Alcohol | 112-72-1 | Kokyo Alcohol Kogyu | 1.00 |
| Hydrogenated Polydecene | 68037-01-4 | Nisshin Oillio | 20.00 |
| Behenyl Alcohol | 661-19-8 | As per current | 3.00 |
| Propylene Glycol | 57-55-6 | Any - not critical | 20.00 |
| PVP (K30) | 9003-39-8 | BASF, Ashlands, Star-Tech | 1.00 |
| Phenoxyethanol & Ethylhexylglycerin (Proprietary blend) | 122-99-6 70445-33-9 | Any - not critical | 0.50 |
| Xanthan Gum | 11138-66-2 | CP Kelco | 0.20 |
| Polyacrylate-1 Crosspolymer (Carbopol Aqua CC Polymer) |  | Lubrizol | 3.00 |
| Aluminum Starch Octenylsuccinate (Dry Flo PC) | 9087-61-0 | Akzo Nobel | 2.00 |
| 25% Citric Acid | 77-92-9 | Any - not critical | 1.20 |
| TOTAL |  |  | 100.00 |

Manufacturing Process

At 100 g scale V1 is 250 ml beaker, V2 is 25 ml beaker and V3 is 50 ml beaker.

Process 100 g Scale:
V1 250 ml beaker: Zn(LBA)2 in situ
Weigh out ZnO
Weigh out LBA (portion to form Zn lactobionate+free lactobionic acid)
  Weigh out 1% NaCl in DI water
  stir to form Zn salt (gentle heat may be used, but process is rapid)
  Weigh out PVP
  stir to form clear solution
V2 25 ml beaker: Aqueous solvent and gels
Weigh out propylene glycol
Weigh out Phenoxyethanol/ethylhexylglycerin,
Weigh out Xanthan gum
disperse Xanthan with spatula, then quickly
Add V2 to V1 with stirring
V3 50 ml beaker: Oils and surfactants
Weigh out hydrogenated polydecene
Weigh out Glucate SS
Weigh out Glucamate SSE-20
Weight out C14 alcohol (Myristyl Alcohol)
Weight out C22 alcohol (Behenyl Alcohol)
Weigh out Dry Flow PC
Mix with spatula to disperse solids.

V3 heat to 60 C and leave for 5 minutes to ensure melting of C22 alcohol

The heat both V1+V2 and V3 to 70° C.-75° C.

Add V3 to (V1+V2) dropwise under low rotor-stator emulsification (low shear, to mix) over 6 minutes (100 g scale); temp ~56 C Mix on maximum shear with Silverson square hole head for 3 minutes (100-200 g scale); temp ~59 C Weigh in Carbomer Aqua CC
Weigh in 25% citric acid pH adjuster
Paddle stir at 150 rpm for 2 minutes to disperse, then at 60 rpm until temperature drops to 30° C.

Measure pH, measure viscosity (at +12-24 hour), pack.

Example 3

Assessment of the Functional Effects of a New Zinc Lactobionate Cream on Skin Surface pH Summary Aim: To establish the effect of a new skin barrier repair composition according to the present invention, referred to herein as an emollient cream formulation containing zinc lactobionate, on skin surface pH.

Method: A Single Open Application Test design with repeated timed skin pH measurements with and without tape-stripping to assess pH changes at deeper layers of the stratum corneum.

Main Findings: (1) The zinc lactobionate test cream according to the present invention exhibits superior (greater reduction of pH, lasting longer and acting deeper down in the stratum corneum) functional effects on skin pH compared to existing products marketed for the treatment of eczema (Diprobase cream and Balneum cream). (2) The zinc lactobionate test cream containing 5% lactobionate in a superior delivery system of the present invention achieves a greater reduction in skin pH, which acts deeper more rapidly, compared to a currently marketed 10% lactobionate cream, which lacks a diffusion coefficient enhancer and doesn't have the optimised delivery system of the present invention.

Processing Equipment Used

Silverson high shear square head on standard Silverson assembly.

1. Introduction

Patients with atopic dermatitis (AD) exhibit elevated skin surface pH. This change in pH is associated with the deterioration of skin barrier function and correlates with the severity of AD. In murine skin, the correction of SC pH improves skin barrier condition, and prevents the emergence of murine AD. The restoration and maintenance of normal skin surface pH is therefore desirable for the improvement of human skin barrier function and the prevention of AD relapses.

The aim of this pilot study was to establish the effect of a new emollient cream formulation containing 5% zinc lactobionate on skin surface pH.

1.1 Objectives

1. To determine the functional effect of a single application of the new 5% zinc lactobionate test cream on skin surface pH over 24 hours.
2. To compare the effects of the 5% zinc lactobionate test cream on skin pH to currently marketed emollient creams for the treatment of eczema
3. To compare the effects of the 5% zinc lactobionate test cream on skin pH to currently marketed lactobionate creams and to an equivalent 5% zinc lactate cream

2. Materials and Methods

2.1 Test Materials

2.2.1 Test Materials for Pilot 1: Batch 1—7 Nov. 2016

| | | | 5% Zinc Lactobionate cream | | |
|---|---|---|---|---|---|
| Function/ Material | Property By process | % w/w 100 g | 1 (Test Form) % w/w 100 g actual #1 Jul. 11, 2016 | 2 (Standard Form) % w/w 100 g actual #2 Jul. 11, 2016 | Comments |
| Active | | | | | |
| ZnO | V1 | 0.10 | 0.1008 | 0.1007 | V1 is 250 ml beaker |
| LBA (1) | V1 | 0.92 | 4.93 | 4.91 | |
| LBA (2) | V1 | 4.00 | | | |
| NaCl 1% in DI water | V1 | 38.32 | 38.08 | 38.34 | |
| Surfactants/ Gelants | | | | | |
| Glucate SS | V3 | 1.26 | 1.2586 | 1.2637 | V3 is 50 ml beaker |
| Glucamate SSE-20 | V3 | 2.52 | 2.5099 | 2.5802 | |
| Glyceryl stearate SD | V3 | 3.48 | 3.4805 | 3.4956 | |
| Oil phase | V3 | | Malc | Malc | |
| ST-E | V3 | 6.00 | 6.0670 | 6.0691 | |
| Hydrogenated polydecene | V3 | 14.00 | 14.0032 | 14.0055 | |
| Dc enhancer 1-tetradecane | V3 | 1.50 | 1.5052 | 1.5076 | 1-tetradecane |
| Dc enhancer MA | V3 | — | — | — | Myrystic acid |
| Ceramide | V3 | — | — | — | |
| Cholesterol | V3 | — | — | — | |
| Linoleic acid | V3 | — | — | — | |
| Cosolvent phase | | | | | |
| Propylene glycol | V2 | 20.00 | 20.0122 | 20.0034 | V2 is 25 ml beaker |
| PVP K25 | V2 | — | — | — | |

-continued

| | | | 5% Zinc Lactobionate cream | | | | |
|---|---|---|---|---|---|---|---|
| Function/ Material | Property By process | % w/w 100 g | 1 (Test Form) % w/w 100 g actual #1 Jul. 11, 2016 | 2 (Standard Form) % w/w 100 g actual #2 Jul. 11, 2016 | | | Comments |
| Preservative | | | | | | | |
| Phe/ethyl hexylglycerin | V2 | 0.50 | 0.4958 | 0.5053 | | | |
| Keltrol CG SFT | V2 | 0.20 | 0.2007 | 0.2028 | | | |
| CACC | V1 + V2 | 4.00 | 4.098 | 4.002 | | | |
| Dry Flow Pure | V3 | 2.00 | 2.0049 | 2.0052 | | | |
| 25% citric A | V1 + V2 | 1.20 | 1.501 | 1.198 | | | |
| total (XL) | | 100.00 | | | | | |
| pH range | | | | | | | |
| actual pH | | | 3.057 | 3.21 | 3.22 | 3.21 | Taken just after man. |
| viscosity #4 @ 6 rpm | | | @ 6 rpm 61 | @ 6 rpm 40 | @ 6 rpm 75 | @ 6 rpm 75 | |

2.2.2 Test Materials for Pilot 2: Batch 2—21 Mar. 2017

| | | 5% Zinc Lactobionate cream | | |
|---|---|---|---|---|
| Function/ Material | By process | % w/w standard 21 Mar. 2017 200 g | % w/w standard 21 Mar. 2017 200 g actual | Comments Manufactured 21 Mar. 2017 17.00 |
| Active | | | | |
| ZnO | V1 | 0.2 | 0.2008 | V1 is 400 ml beaker |
| LBA (1) | V1 | 1.84 | 9.86 | |
| LBA (2) | V1 | 8 | | |
| NaCl 1% in DI water | V1 | 76.64 | 76.49 | |
| Surfactants/ Gelants | | | | |
| Glucate SS | V3 | 2.52 | 2.51 | V3 is 100 ml beaker |
| Glucamate SSE-20 | V3 | 5.04 | 5.04 | |
| Glyceryl stearate SD | V3 | 6.96 | 6.96 | |
| Oil phase | V3 | | | |
| ST-E | V3 | 12 | 12.06 | |
| Hydrogenated polydecene | V3 | 28 | 28.05 | |
| Dc enhancer 1-tetradecane | V3 | 3 | 2.99 | |
| Ceramide | V3 | — | — | |
| Cholesterol | V3 | — | — | |
| Linoleic acid | V3 | — | — | |
| Cosolvent phase | | | | |
| Propylene glycol | V2 | 40 | 40.02 | V2 is 50 ml beaker |
| PVP K25 | V1 | 2 | 2.0042 | |
| Preservative | | | | |
| Phe/ethyl hexylglycerin | V2 | 1 | 1.01 | |
| Keltrol CG SFT | V2 | 0.4 | 0.4022 | |
| CACC | V1 + V2 | 6 | 6.04 | |
| Dry Flow Pure | V3 | 4 | 4.01 | |
| 25% citric A | V1 + V2 | 2.4 | 2.52 | |
| total (XL) | | 200.00 | 200.17 | |
| pH (+25% citric acid) | | | | Measured |
| #1.1 | | | 3.122 | 22 Mar. 17 |
| #1.2 | | | 3.134 | 10.00 |

| Function/Material | By process | | | | | |
|---|---|---|---|---|---|---|
| #1.3 viscosity spindle #4 @ 1.5 rpm | | 3.133 | | | | |

5% Zinc Lactate cream

| Function/Material | By process | % w/w standard 21 Mar. 17 100 g ZnLBA | % w/w standard 21 Mar. 17 100 g ZnLA | % w/w standard 21 Mar. 17 100 g ZnLA | % w/w standard 21 Mar. 17 200 g ZnLA | % w/w standard 21 Mar. 17 200 g ZnLA | Comments Manufactured 21 Mar. 17 17.00 |
|---|---|---|---|---|---|---|---|
| Active | | | | | | | |
| ZnO | V1 | 0.10 | 0.334 | 0.334 | 0.668 | 0.6677 | V1 is 400 ml beaker |
| LBA (1) or LA (1) | V1 | 0.92 | 0.822 | 0.822 | 1.644 | | Hipure 90 |
| LBA (2) or LA (2) | V1 | 4.00 | 4.444 | 4.444 | 8.888 | 10.54 | 10.532 total |
| NaCl 1% in DI water | V1 | 38.32 | 37.74 | 37.34 | 74.68 | 74.70 | |
| Surfactants/Gelants | | | | | | | |
| Glucate SS | V3 | 1.26 | 1.26 | 1.26 | 2.52 | 2.54 | V3 is 100 ml beaker |
| Glucamate SSE-20 | V3 | 2.52 | 2.52 | 2.52 | 5.04 | 5.05 | |
| Glyceryl stearate SD | V3 | 3.48 | 3.48 | 3.48 | 6.96 | 6.96 | |
| Oil phase | V3 | | | | | | |
| ST-E | V3 | 6.00 | 6.00 | 6.00 | 12 | 11.98 | |
| Hydrogenated polydecene | V3 | 14.00 | 14.00 | 14.00 | 28 | 28.01 | |
| De enhancer 1-tetradecane | V3 | 1.50 | 1.50 | 1.50 | 3 | 3.00 | |
| Ceramide | V3 | — | — | — | — | | |
| Cholesterol | V3 | — | — | — | — | | |
| Linoleic acid | V3 | — | — | — | — | | |
| Cosolvent phase | | | | | | | |
| Propylene glycol | V2 | 20.00 | 20.00 | 20.00 | 40.00 | 40.02 | V2 is 50 ml beaker |
| PVP K25 | V1 | 1.00 | 1.00 | 1.00 | 2.00 | 2.0017 | |
| Preservative | | | | | | | |
| Phe/ethyl hexylglycerin | V2 | 0.50 | 0.50 | 0.50 | 1.00 | 1.00 | |
| Keltrol CG SFT | V2 | 0.20 | 0.20 | 0.20 | 0.40 | 0.4004 | |
| CACC | V1 + V2 | 3.00 | 3.00 | 3.00 | 6.00 | 6.05 | |
| Dry Flow Pure | V3 | 2.00 | 2.00 | 2.00 | 4.00 | 4.00 | |
| 25% citric A | V1 + V2 | 1.20 | 1.20 | — | — | | |
| 18% KOH drops | V1 + V2 | | | 1.60 | 3.20 | 3.20 | |
| total (XL) | | 100 | 100 | 100 | 200.00 | 200.12 | |
| pH (+KOH) | | | | | | | Measured |
| #1.1 | | | | | | 3.274 | 22 Mar. 2017 |
| #1.2 | | | | | | 3.280 | 10.00 |
| #1.3 | | | | | | 3.271 | |
| viscosity spindle #4 @ 1.5 rpm | | | | | | nd | |

2.2 Test Design

Figure 1:
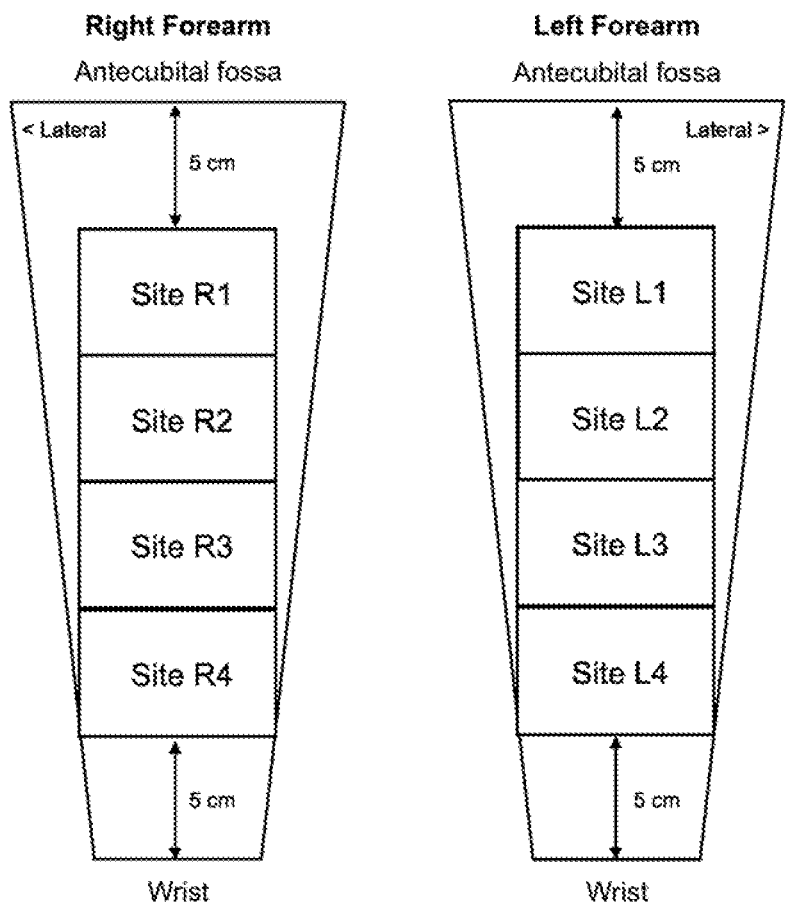
FIG. 1 shows treatment study sites on the arm of study participants in Example 3

A single open-application test was performed as previously described (Danby SG, Brown K, Higgs-Bayliss T et al. The Effect of an Emollient Containing Urea, Ceramide NP, and Lactate on Skin Barrier Structure and Function in Older People with Dry Skin. *Skin Pharmacol Physiol* 2016; 29: 135-47). In this instance, there were up to four treatment sites per arm in each participant, providing up to eight test sites in total (FIG. 1). Each test site measured 5-7 cm by 4 cm. After baseline measurements of skin surface pH, ½ fingertip unit of the required emollient cream/test formulation was applied to the appropriate test site. The creams were gently spread across the test sites using a gloved finger (glove was changed between treatments). Following treatment, measurements were repeated at timed intervals. There were 2 participants in total with healthy skin.

To assess the effects on pH beneath the skin surface tape stripping was performed to remove corneocyte layers and expose deeper layers of the stratum corneum at set time points following the single application of the test creams. All test sites were wiped with a dry tissue prior to tape stripping to remove any residues. pH measurements were repeated after each individual tape-strip. Tape stripping was performed at separate sites to those used for the time course measurements.

2.3 Statistical Analysis

All graphs were prepared using Prism 6 (GraphPad Software, La Jolla, USA). No statistical analysis was performed, as the results are pilot data obtained from 2 participants. All values are expressed as means±standard error of the mean (SEM).

3. Results and Discussion

Figure 2:
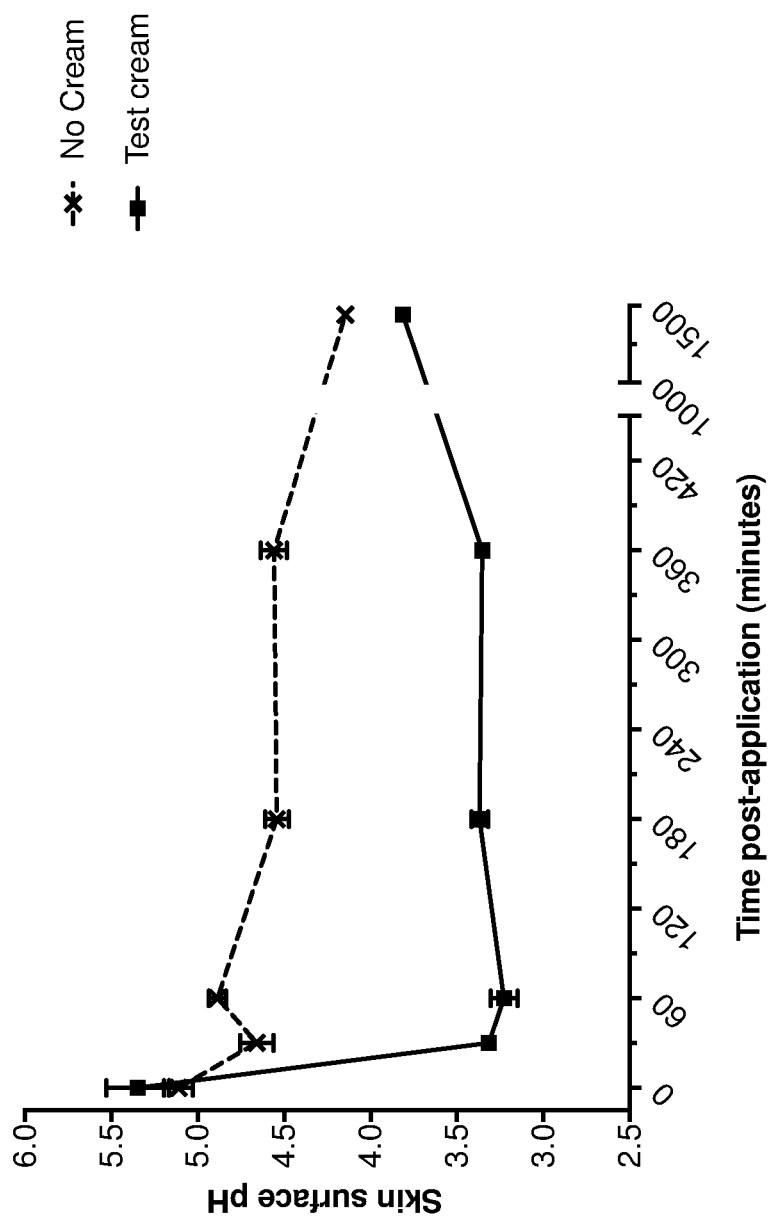
FIG. 2 illustrates the effects of the test cream on skin surface pH over 24 hours following a single application.

3.1 Objective 1: Effect of a New Zinc Lactobionate Emollient Cream on Skin Surface pH A new skin barrier repair emollient cream (the test cream, cream #2) containing 5% zinc lactobionate and a diffusion coefficient enhancer, 1-tetradecane, has been produced with the aim of bringing skin surface pH down between 3.0 and 3.5 units in support of optimum skin physiological processes. FIG. 2 illustrates the effects of the test cream on skin surface pH over 24 hours following a single application. The test cream appreciably reduced skin surface pH to below 3.5 units, when compared to an untreated control site displaying a pH above 4.5 units, for more than 6 hours. The effect on skin surface pH was diminished after 24 h and it is not clear from this dataset how long beyond 6 hours skin surface pH is reduced.

3.2 Objective 2: The effects of the Zinc Lactobionate Test Cream on Skin pH Compared to Currently Marketed Emollient Creams for the Treatment of Eczema A further single application test was performed to assess the effects of the test cream on surface pH between 6 and 24 h following application, and provide a comparison with some emollient creams currently marketed for eczematous conditions.

Figure 3:
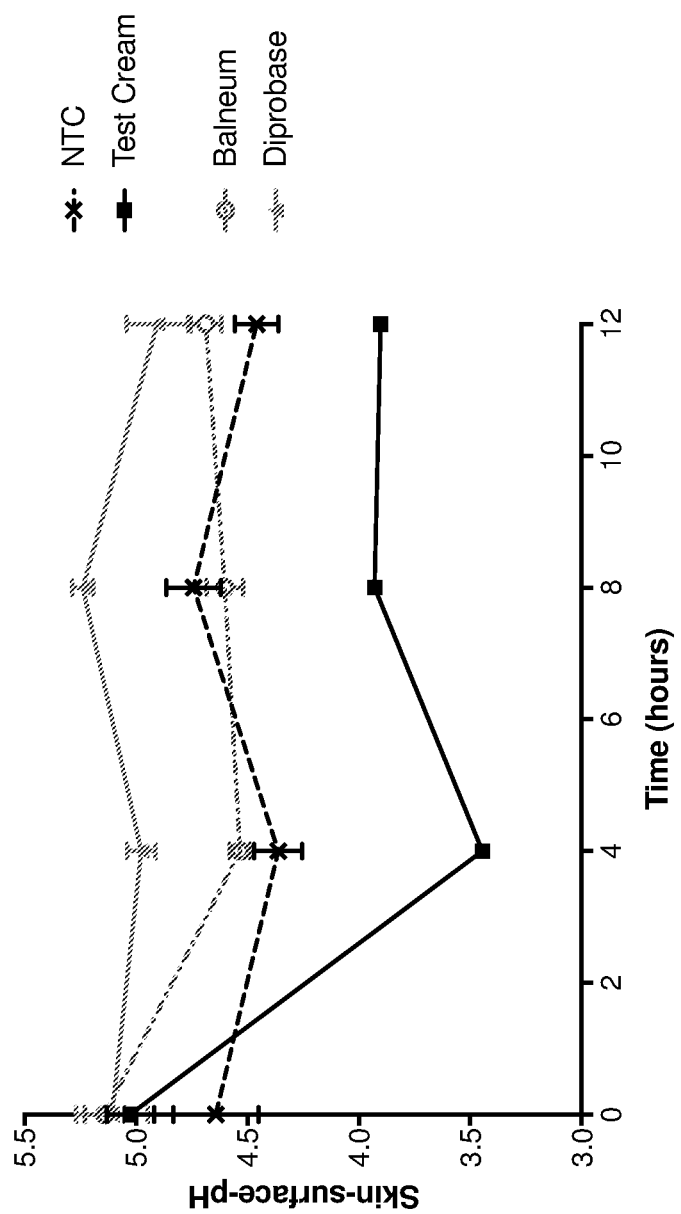
FIG. 3 illustrates the effects of the test cream on skin surface pH compared to Diprobase cream (an emollient only cream) and Balneum cream (a lactic acid containing product).

FIG. 3 illustrates the effects of the test cream on skin surface pH compared to Diprobase cream and Balneum cream. Diprobase cream, a simple occlusive emollient, is one of the most widely prescribed topical treatments for eczema. Balneum cream contains 5% urea, lactic acid and lactate and has previously been shown to significantly reduce skin surface pH when compared to a panel of currently marketed products for eczema (Danby S G, Brown K, Higgs-Bayliss T et al. as above). As expected Diprobase maintains skin surface pH at a relatively high level, above pH 5.0. Balneum cream on the other hand reduced skin surface pH down to approximately pH 4.5, and kept skin surface pH below 5.0 for the duration of the test. The zinc lactobionate test cream achieved the greatest reduction in skin surface pH (down to pH 3.5) for the longest period of time.

Figure 4:
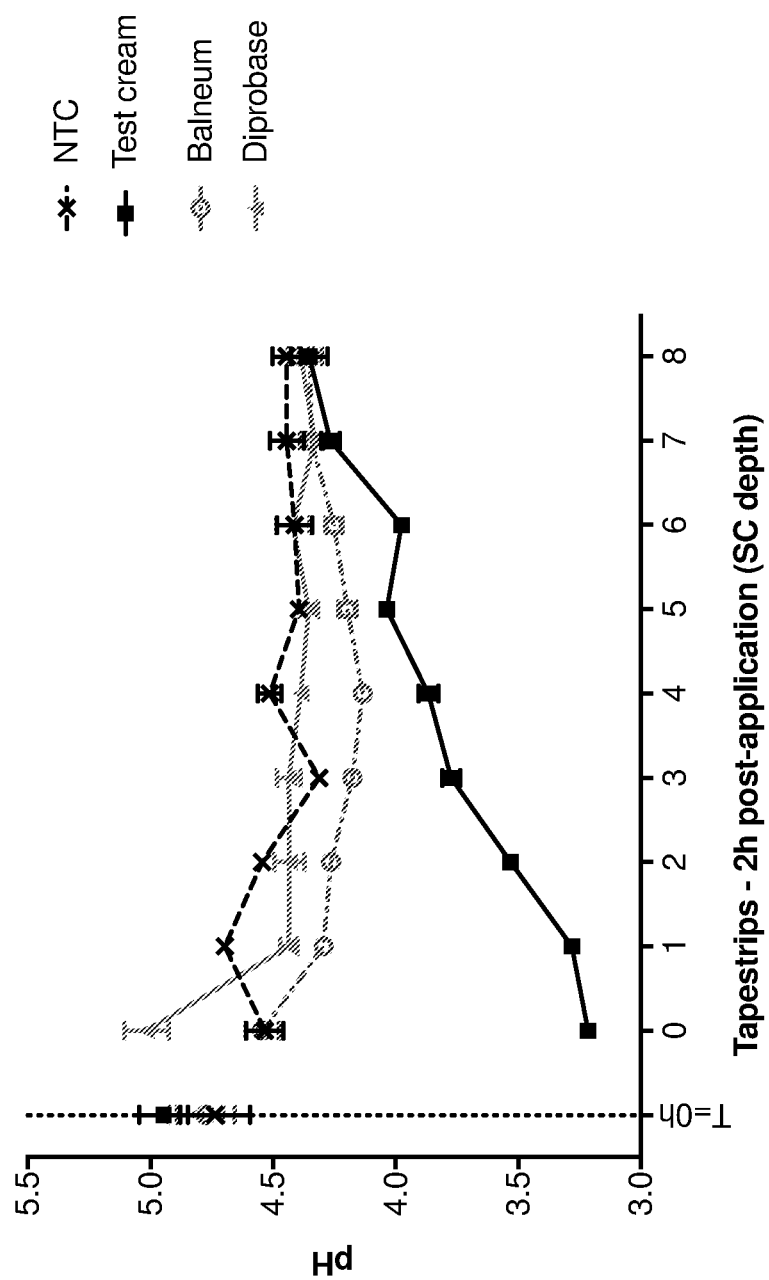
FIG. 4 shows the change in skin pH throughout the stratum corneum (SC) 2 hours following a single application of the test cream compared to Diprobase cream, (an emollient only cream), Balneum cream (a lactic acid containing product) and a no treatment control (NTC) in a participant with healthy skin.

To determine the effect of the test cream on pH under the surface of the skin (through the stratum corneum) tape-stripping was performed 2 h post-application (FIG. 4).

In the absence of treatment, pH measurements remained fairly stable at around 4.5 units following the removal of tape-strips 1-8 (each removing between 0-3 corneocyte layers) to access deeper layers of the stratum corneum. On sites receiving Diprobase, pH dropped sharply after removal of the first tape-strip. As this first tape-strip is expected to remove the majority of surface residues from the cream, this suggests that the effects of Diprobase, at increasing skin surface pH, are restricted to the surface of the skin. Application of Balneum cream was associated with a slight reduction in pH deeper down into the stratum corneum. By far the greatest reduction in skin surface pH was observed for the test cream however, demonstrating the ability of the formulation to modify stratum corneum pH beneath the surface. The reduction in pH was maximal at the surface and steadily normalised over 7 tape-strips.

Taken together the new 5% zinc lactobionate skin barrier repair cream of the present invention, with its novel delivery system, displays a very promising ability to modify stratum corneum pH (both on and below the surface) to a greater extent and for a longer period of time compared to currently marketed emollient creams for the treatment of eczema.

3.3 Objective 3: The Effects of the Zinc Lactobionate Test Cream on Skin pH Compared to Currently Marketed Lactobionate Topical Products and to an Equivalent Zinc Lactate Cream In the subsequent tests the functional effects of the 5% zinc lactobionate test cream on skin pH are compared with two existing lactobionate products (not marketed for eczema) and the test cream formulated with 5% zinc lactate instead of zinc lactobionate. Diprobase cream was included as a reference topical cream prescribed for eczema. There are very few lactobionate products available and so one of the products is a cream with 10% lactobionate and no diffusion coefficient enhancer ("10% Lactobionate Cream") and the other is a wash product, as opposed to a topical product ("Intimate Creamy Wash"). Following application all products absorbed readily into the skin, with the exception of the marketed 10% lactobionate topical cream, which left an unpleasant flaky white residue on the surface. The zinc lactate test cream induced a stinging sensation either immediately or with a slight delay following application. A sensation of pain/stinging was experienced with each subsequent pH measurement (which involves contacting a wet glass probe to the skin surface). No sensation was reported for any of the other products under the conditions of this test.

FIG. 5 illustrates the effects of a single application of the creams studied on skin surface pH over 12 hours. In agreement with the previous test, Diprobase cream had no significant effect on skin surface pH. The intimate creamy wash, containing an unknown amount of lactobionate, reduced skin surface pH by approximately 0.5 units for between 6 and 8 hours. The 10% lactobionate topical cream had a more pronounced effect, reducing surface pH by about 1.5 units 2 hours after application, and maintaining reduced surface pH for the duration of the test. The test creams brought above the greatest reduction in skin surface pH, by approximately 2 pH units, regardless of whether they were formulated with lactate or lactobionate. Moreover the lower level of pH was maintained for the 12-hour duration of the test. It is interesting to note that the test creams contain half the level of acid found in the marketed 10% lactobionate cream (5% compared to 10% in the marketed lactobionate topical cream), and yet still elicited a greater reduction in skin surface pH. This suggests that the improved delivery system of the test cream, comprising a diffusion coefficient enhancer in addition to a penetration enhancer, significantly enhances the functional effects on skin surface pH.

Substitution of lactobionate with lactate did not appear to alter the functional effects of the test cream on skin surface pH. Based on the marked difference in skin sensation, with the lactate cream eliciting a stinging/burning sensation upon application, the lactobionate cream was put forward for further testing compared to the marketed 10% lactobionate cream.

The effects of the lactobionate test cream compared to the marketed 10% lactobionate cream on pH throughout the stratum corneum were assessed by tape-stripping at 2 hours following application. At 2 hours post application the treated sites all displayed significantly reduced surface pH (FIG. 6). The effects of both creams persisted to deeper layers of the stratum corneum, with the test zinc lactobionate cream displaying the deepest effects. The fact that the 5% lactobionate test cream achieves a greater reduction in skin pH deeper down compared to the 10% lactobionate cream, despite its lower lactobionate content, suggests that the test formulation contributes to the functional effects observed on skin pH.

4. Conclusions

The zinc lactobionate test cream with novel delivery system displays an ability to reduce skin surface pH down to between 3.0 and 3.5 units, and maintain low skin surface pH for more than 12 hours following application.

The zinc lactobionate test cream exhibits superior (greater reduction of pH, lasting longer and acting deeper down in the stratum corneum) functional effects on skin pH compared to existing products marketed for the treatment of eczema (Diprobase cream and Balneum cream)

The zinc lactobionate test cream containing 5% lactobionate achieves a greater reduction in skin pH, which acts deeper more rapidly, compared to a currently marketed 10% lactobionate cream suggesting that it has a superior delivery system.

The new test cream exhibits similar effects on skin surface pH irrespective of whether lactic acid or lactobionic acid is used in the formulation, however the lactic acid variant of the formulation is associated with an unpleasant burning/stinging sensation upon application and the lactobionate variant is not.

Example 4

A Comparison of Perceived Irritation/Pain Sensation Arising from Topical Application of Creams Containing Lactic Acid and Lactobionic Acid This experiment tested a composition of the present invention, an exemplary skin barrier cream comprising lactobionate, for any perceived irritation or pain sensation arising from topical application. For comparison purposes the same cream formulation was prepared in which the lactobionate was absent and was replaced by lactate and this cream was tested for any perceived irritation or pain sensation arising from topical application.

Introduction

Creams and emollients incorporating lactic acid are currently used for moisturising skin and in some cases for the treatment of atopic dermatitis. However, a negative reported for lactic acid creams, particularly applied to compromised skin, is 'irritation' following application. A telling comment from a leading dermatologist was a child suffering eczema referring to the prescribed lactate containing cream as "the stingy cream".

There has been some debate on the extent to which the irritation arising from lactate containing creams is a consequence of the low acidic pH or the lactate molecule itself. The influence of formulation on severity has also been raised. For example, is perceived irritation more noticeable with formulations that are more effective in enhancing skin penetration?

Any negatives associated with creams and emollients directed for topical conditions are clearly undesirable, and they can seriously effect clinical outcome through reduced patient compliance. As lactate containing creams have been shown to deliver benefits in treating dry skin and atopic dermatitis it would clearly be beneficial to be able to deliver these benefits effectively, but without undesirable sensation.

The present study investigates the pain sensation experienced for two creams differing only their chosen therapeutic ingredient, namely zinc lactate vs zinc lactobionate

Materials and Methods

Topical creams were supplied by Limeway Consultancy Ltd. The base formulation of both products was essentially identical (see the Tables in section 2.2.2 above). The two creams were:

Zinc Lactate 5% w/w pH 3.2, and
Zinc Lactobionate 5% w/w, pH 3.2

The subject used in the test was Male, Age 58, with no previous history of any adverse reaction to any topical products.

For testing of irritation, the volar forearm close to the flex region was selected on both arms of the subject. A plastic template incorporating a 20 mm diameter hole was pressed against the skin and the area of exposed skin then subject to twenty successive tape-strips (Sellotape Original Golden). The aim in this procedure was to compromise the skin by reducing the stratum corneum barrier and create a situation closer to that expected in such conditions as atopic eczema.

After tape stripping, a period of three hours was allowed to elapse in order to allow any sensation experienced during tape-stripping to subside.

Creams were applied liberally by forefinger to the test areas on both arms of the subject such that residual cream was still present post application. Both creams were identical in appearance and the subject was not aware which cream contained which zinc salt i.e. the study was blind.

Following application of the products the subject recorded any negative sensations experienced using a Labeled Magnitude Scale (LMS) which has the advantage over basic line-scales of incorporating semantic descriptors. (FIG. 7)

Scoring was made at the following intervals of time: On application, 1 min, 2 min, 5 min, 15 min, 30 min, 1 hr, 3 hr, and 6 hr.

During the period of the test the subject remained seated with the test areas remaining exposed at a room temperature of approx 20 degrees centigrade. The subject was allowed to read paperwork but not allowed any mechanical contacts with the test areas.

Results

Zinc Lactate 5% Cream pH 3.2

Initially the subject only experienced a mild cooling sensation, presumably arising from evaporation of water and other volatiles from the formulation i.e. latent heat of evaporation effect. However subsequently the subject began to perceive irritation and burning sensation which gradually became a stinging sensation similar in nature to a nettle sting. This gradually died down into an irritating mild burning sensation which persisted with diminishing intensity until it was barely detectable at the three hour point.

The profile of the sensation experience is shown in FIG. 8. At peak the pain was noted as having occasional sharp stings, not seriously painful but noticeably distinct. After the perceived peak of sensation the sensation was considered primarily as annoying rather than debilitating but noticeably persistent. The likely consequences of applying such a cream to a child with eczema before bedtime were apparent.

Zinc Lactobionate 5% Cream, pH 3.2

As with the zinc lactate cream, the initial sensation experienced was one of mild cooling. However, beyond that no pain or irritation whatsoever was perceived.

Discussions

Both the creams used in this study were formulated at the same pH and both have been shown to have similar effects on skin pH when applied topically. The base formulation used in this study has also been shown to be effective in enhancing penetration of both zinc lactate and zinc lactobionate.

Very Surprisingly, in spite of these similarities, zinc lactate 5% leads to a stinging/burning sensation for some time after application to compromised skin, whereas zinc lactobionate does not generate any perceived negative sensations post application. Clearly in terms of encouraging patient compliance a cream containing zinc lactobionate represents a significant advancement over a zinc lactate cream in terms of avoiding negative sensations.

Conclusions

In a formulation tailored for effective delivery into skin, zinc lactobionate 5% cream pH 3.2 does not generate any perceivable pain or burning following application to tape-stripped compromised skin.

In an identical formulation, zinc lactate 5% pH 3.2 generates perceivable stinging/burning sensation for more than an hour after application to tape-stripped compromised skin.

The present study indicates that zinc lactobionate represents a significantly better therapeutic agent than zinc lactate in terms of avoidance of negative pain sensation and the compromising of patient compliance.

Example 5

Testing of Robustness and Physical Stability of Exemplary Compositions of the Present Invention Towards the end of the formulation design process, the formulation proposed for further development (sample #1) and four variants of this (samples #2-#5), in which critical excipient levels were varied, were subject to three-cycle freeze-thaw physical stability testing. The outline stability protocol is a shown below. Three-cycle freeze-thaw testing is a standard test to ensure physical stability of topical dermatological products.

Earlier formulations, data not shown, exhibited poor physical stability, hypothesised to be due to solubilisation of the high HLB Glucamate SSE-20 by lactobionic acid from the emulsion interface into the continuous aqueous-glycol phase. In all five test samples studied here the ratio of Glucamate SSE-20:Glucate SS was increased to 2:1 and NaCl was added to "salt-out" the Glucamate SSE-20. Interestingly, no examples of dispersed systems of lactobionic acid with both Glucamate SSE-20 and Glucate SS could be found in the literature. Several lactobionic acid products, for example Face Essentials 10% lactobionic acid cream contain Glucate SS (INCI Methyl Glucose Sesquistearate) only.

| Day 1 15.00 am | Day 2 15.00 am | Day 3 15.00 am | Day 4 15.00 am | Day 5 15.00 am | Day 6 15.00 am | Day 7 15.00 am | Day 8 15.00 am | Day 9 15.00 am | Day 10 15.00 am | Day 11 15.00 am | Day 12 15.00 am |
|---|---|---|---|---|---|---|---|---|---|---|---|
| Initials Freezer | RT | 45C | RT Finals | Initials Freezer | RT | 45C | RT Finals | Initials Freezer | RT | 45C | RT Finals |
| C1 | C1 | C1 | C1 | C2 | C2 | C2 | C2 | C3 | C3 | C3 | C3 |
| Date 24 Nov. 2016 | 25 | 26 | 27 | 28 | 29 | 30 | 1 | 2 | 3 | 4 | 5 |

Two samples of each of the five formulations were studied over three-cycle freeze-thaw and a further control sample of each was kept at 20° C. Initial and final appearance, pH and viscosity were recorded, as shown below.

Viscosities at final assessment on day #12 (rheometer spindle #4 1.5 rpm).

| Sample | Condition | V#1 | V#2 | V#3 | Mean n = 3 | Initial V | pH | Comment |
|---|---|---|---|---|---|---|---|---|
| #1.1 | 45 FThaw | 45.0 | 45.0 | 45.0 | 45.00 | nt | 3.172 | |
| #1.2 | 45 FThaw | 45.0 | 46.0 | 49.0 | 46.67 | 40.33 | 3.184 | 3.175 |
| #1.3 | Lab temp | 47.5 | 47.5 | 53.0 | 49.33 | nt | 3.188 | |
| #2.1 | 45 FThaw | 45.0 | 43.5 | 43.5 | 44.00 | nt | 3.120 | |
| #2.2 | 45 FThaw | 48.0 | 45.5 | 49.0 | 47.50 | 33.33 | 3.117 | 3.144 |
| #2.3 | Lab temp | 44.0 | 41.0 | 41.5 | 42.17 | nt | 3.123 | |
| #3.1 | 45 FThaw | 35.0 | 36.0 | 32.0 | 34.33 | nt | 3.086 | |
| #3.2 | 45 FThaw | 41.50 | 40.5 | 39.5 | 40.50 | 31.83 | 3.084 | 3.127 |
| #3.3 | Lab temp | 38.0 | 38.0 | 37.0 | 37.67 | nt | 3.088 | |
| #4.1 | 45 FThaw | 42.0 | 45.5 | 42.5 | 43.33 | nt | 3.166 | |
| #4.2 | 45 FThaw | 41.0 | 42.0 | 40.5 | 41.17 | 44.33 | 3.166 | 3.198 |
| #4.3 | Lab temp | 51.0 | 49.0 | 53.0 | 51.00 | nt | 3.172 | |
| #5.1 | 45 FThaw | 46.0 | 45.0 | 49.0 | 46.67 | nt | 3.191 | |
| #5.2 | 45 FThaw | 49.0 | 49.50 | 48.0 | 48.83 | 58.50 | 3.191 | 3.209 |
| #5.3 | Lab temp | 63.5 | 57.0 | 64.0 | 61.50 | nt | 3.194 | |

At the end of the study, some changes in viscosity were noted between free-thaw and 20° C. samples in which surfactant levels were increased by 12.5% and 25% (samples #4 and #5).

Storage at 45° C., just below the melting point of the glyceryl stearate wax, caused, as expected, some slight change in appearance-texture with an apparent slight thickening of samples #2 and #3. No significant changes in viscosity or pH were observed with sample #1, which was selected for further development.

| Sample | Condition | Comment Jun. 12, 2016 |
|---|---|---|
| #1.1 | 45° F. Thaw | No syneresis, very slight granular texture |
| #1.2 | 45° F. Thaw | No syneresis, very slight granular texture |
| #1.3 | Lab temp | white soft smooth textured cream |
| #2.1 | 45° F. Thaw | No syneresis, slightly thicker than RT, very slight granular texture |
| #2.2 | 45° F. Thaw | No syneresis, slightly thicker than RT, very slight granular texture |
| #2.3 | Lab temp | white soft smooth textured cream |
| #3.1 | 45° F. Thaw | No syneresis, slightly thicker than RT, very slight granular texture |
| #3.2 | 45° F. Thaw | No syneresis, slightly thicker than RT, very slight granular texture |
| #3.3 | Lab temp | white soft smooth textured cream |
| #4.1 | 45° F. Thaw | No syneresis, thicker than RT, very slight granular texture |
| #4.2 | 45° F. Thaw | No syneresis, thickener than RT, very slight granular texture |
| #4.3 | Lab temp | white soft smooth textured cream |
| #5.1 | 45° F. Thaw | No syneresis, thickeness as RT, texture as RT |
| #5.2 | 45° F. Thaw | No syneresis, thickeness as RT, texture as RT |
| #5.3 | Lab temp | white softish smooth textured cream |

Actual Batch Sheets: Compositions Tested

| Function/ Material | By process | % w/w 100 g standard DHFN #1.1 changes | % w/w 100 g standard DHFN #1.2 changes | % w/w 100 g standard DHFN #1.3 changes | % w/w 100 g standard DHFN #1.4 changes | % w/w 100 g standard DHFN #1.5 changes | Comments |
|---|---|---|---|---|---|---|---|
| Active | | | | | | | |
| ZnO | V1 | 0.10 0.1012 | 0.10 0.1008 | 0.10 0.1014 | 0.10 0.1013 | 0.10 0.1012 | V1 is 250 ml beaker |
| LBA (1) | V1 | 0.92 | 0.92 | 0.92 | 0.92 | 0.92 | |
| LBA (2) | V1 | 4.00 4.92 | 4.00 4.92 | 4.00 4.93 | 4.00 4.93 | 4.004.92 | |
| NaCl 1% in DI water | V1 | 38.32 38.35 | 40.82 40.82 | 43.32 43.32 | 37.41 37.43 | 36.50 36.53 | |
| Surfactants/ Gelants | | | | | | | |
| Glucate SS | V3 | 1.26 1.2640 | 1.26 1.2605 | 1.26 1.2663 | 1.42 1.4182 | 1.57 1.5779 | V3 is 50 ml beaker |
| Glucamate SSE-20 | V3 | 2.52 2.5191 | 2.52 2.5373 | 2.52 2.5213 | 2.83 2.8869 | 3.16 3.1708 | |
| Glyceryl stearate SD | V3 | 3.48 3.4788 | 3.48 3.4788 | 3.48 3.4722 | 3.92 3.9200 | 4.35 4.3545 | |
| Oil phase | V3 | | | | | | |
| ST-E | V3 | 6.00 6.1381 | 6.00 6.586 | 6.00 6.0998 | 6.00 6.0769 | 6.00 6.083 | |
| Hydrogenated polydecene | V3 | 14.00 14.0104 | 14.00 14.0228 | 14.00 14.0231 | 14.00 14.0265 | 14.00 14.0226 | |
| Dc enhancer Malc | V3 | 1.50 1.5172 | 1.50 1.5000 | 1.50 1.5064 | 1.50 1.5067 | 1.50 1.5013 | |
| Ceramide | V3 | — | — | — | — | — | |
| Cholesterol | V3 | — | — | — | — | — | |
| Linoleic acid | V3 | — | — | — | — | — | |
| Cosolvent phase | | | | | | | |
| Propylene glycol | V2 | 20.00 20.0424 | 17.50 17.5028 | 15.00 15.0090 | 20.00 20.0092 | 20.00 20.0072 | V2 is 25 ml beaker |
| PVP K25 | V1 | 1.00 1.0009 | 1.00 1.0015 | 1.00 1.0024 | 1.00 1.0003 | 1.00 1.0016 | |
| Preservative | | | | | | | |
| Phe/ethyl hexylglycerin | V2 | 0.50 0.5132 | 0.50 0.5158 | 0.50 0.4929 | 0.50 0.5153 | 0.50 0.5000 | |
| Keltrol CG SFT | V2 | 0.20 0.2013 | 0.20 0.2004 | 0.20 0.2082 | 0.20 0.2018 | 0.20 0.2025 | |
| CACC | V1 + V2 | 3.00 3.164 | 3.00 2.98 | 3.00 3.071 | 3.00 3.012 | 3.00 3.045 | |
| Dry Flow | V3 | 2.00 | 2.00 | 2.00 | 2.00 | 2.00 | |

-continued

| Function/ Material | By process | % w/w 100 g standard DHFN #1.1 changes | % w/w 100 g standard DHFN #1.2 changes | % w/w 100 g standard DHFN #1.3 changes | % w/w 100 g standard DHFN #1.4 changes | % w/w 100 g standard DHFN #1.5 changes | Comments |
|---|---|---|---|---|---|---|---|
| Pure 25% citric A | V1 + V2 | 2.0047 1.20 1.186 | 2.0584 1.20 1.222 | 2.0715 1.20 1.233 | 2.0011 1.20 1.212 | 2.0031 1.20 1.216 | |
| total (XL) | | 100.00 | 100.00 | 100.00 | 100.00 | 100.00 | |
| actual pH | | 3.175 | 3.144 | 3.127 | 3.198 | 3.209 | |
| viscosity #4 @ 1.5 rpm | | 40 43 38 | 33 32.5 34.5 | 28 35 32.5 | 42 45 46 | 59 59 57.5 | all sample #x.2 |
| Appearance | | 40.33 | 33.33 | 31.83 | 44.33 | 58.50 | |

Example 6

Consumer Testing of the Perceived Properties of a Composition of the Present Invention This example provides a consumer perception comparison study between a skin barrier cream of the present invention and a commonly used aqueous cream BP.

Introduction

Skin creams and emollients intended for use on severe dry skin and conditions such as eczema are often considered as being quite unpleasant to use. Descriptors such as sticky, greasy, too thick etc are quite commonly voiced for such creams. Whilst clinically such creams have potential therapeutic benefits, such benefits can only be realised if they are used effectively i.e. there is good compliance. Where products are unpleasant to use, full compliance is inevitably less likely.

Intended for application in the treatment of severe dry skin, eczema and related conditions, we have developed a Zinc Lactobionate cream designed to deliver not only improved efficacy, but also far better user experience when compared against most current marketed creams and emollients in the sector.

Reported here is a brief study concerned specifically with collecting data on the perceived in-use and after-use properties of the Zinc Lactobionate cream, and a comparison against the perceived properties of a widely used marketed emollient 'Aqueous Cream BP' which has often been a benchmark used in eczema clinical studies.

The key objectives of the study were:
To gain an insight into the consumer perceived, in-use, attributes of the Zinc Lactobionate product.
To compare the perceived attributes against a standard marketed emollient Aqueous Cream BP.
To establish which of the two products tested was most preferred overall.

Study Protocol

A full 'Study Protocol' was prepared for this investigation, compiled in the spirit of GCP (good clinical practice) even though this was essentially a cosmetic consumer perception study. (Full 'Study Protocol' on file)

Study Subjects: Three volunteers were used in this pilot study.

| Sex | Age Range | Self-Reported Skin Type |
|---|---|---|
| Female | 36-55 | Combination |
| Female | 18-25 | Combination |
| Male | 26-35 | Combination |

None of the subjects had previously suffered any adverse event using topical skin-care or medicinal products.

Test Products: Two products were used in this study
Zinc Lactobionate 5% cream ex Limeway Consultancy Limited
Aqueous Cream BP ex Tesco Pharmacy.

Study Methods

This was a supervised study in so far as a supervisor briefed volunteers and subsequently presented the products for testing. Subjects were not aware of the identity of the products, simply that they were skin-care creams.

Subjects were first individually briefed on the nature of the study and their 'informed consent' received. No subject had any vested interest in the products, or the study outcome.

Subjects were told that they would be presented with two different topical creams both of which were intended for use on severe dry skin or conditions such as eczema. The creams could in principle be applied to skin on any part of the body, but in the present study they would be applying product to their volar forearm. Following use of the creams they would be asked a series of simple questions on how they perceived the creams. Subjects were then given a questionnaire (Appendix 1) and allowed to study the questions at least 24 hours ahead of testing.

On the day of testing subjects were asked to expose both their volar forearms and were presented with two pea-sized amounts of the test creams on a large flat plastic spatula with the creams labelled alongside as C and H. They were then asked to take whichever cream they wanted to use first with their index finger and then rub the product onto their opposite volar forearm. Having tested one cream they then moved onto the second cream repeating the process on their other arm. Immediately after testing both creams they completed the questionnaire.

Results

The results of the study are shown in Table 1. Data relates solely to user 'perception' in the context of their personal likes and dislikes. No adverse events were reported.

Aqueous Cream BP

The key perceived properties for this cream can be briefly summarised:
  Good at moisturising
  Quite difficult to rub into the skin
  Some or much difficulty being absorbed by the skin
  Residue on the skin was a little greasy
  The skin was left a little or quite refreshed
  The product felt quite unpleasant to use
  Overall pleasantness was considered reasonable to poor

TABLE 1

Perceived Properties of Zinc Lactobionate Cream and Aqueous Cream BP

|  | PRODUCT C Aqueous Cream BP | PRODUCT H Zinc Lactobionate |
|---|---|---|
| MOISTURISING | | |
| Subject 1 (Female, 36-55 yrs) | Good | Very Good |
| Subject 2 (Female, 18-25 yrs) | Good | Very Good |
| Subject 3 (Male, 26-35 yrs) | Good | Good |
| TEXTURE-THICKNESS | | |
| Subject 1 | Neither/Nor | Neither/Nor |
| Subject 2 | Much Too Thick | Neither/Nor |
| Subject 3 | Much Too Thick | Neither/Nor |
| GETTING IT INTO SKIN | | |
| Subject 1 | Quite Difficult | Very Easy |
| Subject 2 | Quite Difficult | Very Easy |
| Subject 3 | Quite Difficult | Very Easy |
| ABSORBED BY SKIN | | |
| Subject 1 | Some Difficulty | Very Easily |
| Subject 2 | Some Difficulty | Very Easily |
| Subject 3 | Much Difficulty | Very Easily |
| RESIDUE ON SKIN | | |
| Subject 1 | A Little Greasy | No Residue |
| Subject 2 | A Little Greasy | No Residue |
| Subject 3 | A Little Greasy | No Residue |
| SENSATION LEFT | | |
| Subject 1 | Quite Refreshed | Quite Refreshed |
| Subject 2 | Quite Refreshed | Very Refreshed |
| Subject 3 | A Little Refreshed | Quite Refreshed |
| FEEL TO USE | | |
| Subject 1 | Quite Unpleasant | Very Pleasant |
| Subject 2 | Quite Unpleasant | Very Pleasant |
| Subject 3 | Quite Unpleasant | Quite Pleasant |
| OVERALL PLEASENTNESS | | |
| Subject 1 | Poor | Very Good |
| Subject 2 | Reasonable | Very Good |
| Subject 3 | Poor | Good |
| PREFERRED PRODUCT | | |
| Subject 1 | | X |
| Subject 2 | | X |
| Subject 3 | | X |

Zinc Lactobionate Cream

The key perceived properties for this cream can be briefly summarised:
  Good or very good at moisturising
  It was neither too thick nor too runny
  Very easy to rub into the skin
  Very easily absorbed by the skin
  It left no greasy residue on the skin
  The skin was left quite or very refreshed
  The product felt quite or very pleasant to use
  Overall pleasantness of the product was perceived as good or very good

Subject Comments

Where subjects chose to leave comments these were as follows.

Subject 1: Product C—Dislike—Difficult to rub into the skin
  Product H—(No comment)
Subject 2: Product C—Dislike—A bit thick
  Product H—Like—Felt smooth
Subject 3: Product C—Dislike—Long time to absorb, bit like sun cream.
  Product H—Like—Was absorbed very quickly.

All comments and feedback on the Aqueous Cream BP product tended to be negative. The reverse was true for the Zinc Lactobionate cream, with all comments and feedback being positive.

Overall Preference

Although this study was not primarily intended as a 'preference test', subjects were unanimous in preferring the Zinc Lactobionate cream over Aqueous Cream BP.

Discussions and Conclusions

With the subject numbers involved, the present study was intended primarily to identify strong perceived characteristics and identify any 'gross negatives'. The study confirmed much informal feedback that the Zinc Lactobionate Cream is perceived as having many positive attributes and is pleasant to use. Commonly used Aqueous Cream BP was by comparison far less preferred. From a patient perspective, Zinc Lactobionate cream would be expected to improve compliance.

Overall

Zinc Lactobionate cream was perceived as having many positive attributes and no negatives. In particular it was found to penetrate skin very well, was readily absorbed and left no greasy residue.

Zinc Lactobionate cream was importantly considered pleasant to use, and much preferred over a product such as Aqueous Cream BP.

Example 6 - APPENDIX 1
CONSUMER STUDY QUESTIONNAIRE

Questionnaire - Part 1A
CREAMS H and C

*Please complete the questionnaire and return to the supervisor*

PLEASE CIRCLE THE NUMBER AGAINST THE ANSWER FOR EACH QUESTION THAT BEST REFLECTS YOUR OPINION

Please answer Q1-3 before using the product(s).

1. Please circle the number of your age group
- 18-25 years  1
- 26-35 years  2
- 36-55 years  3
- 56+ years  4

2. Please indicate what type of skin you have
- Dry  1
- Normal  2
- Oily  3
- Sensitive  4
- Combination  5

3. Do you use a skin care product for dry, cracked or inflamed skin.
- Yes  1
- No  2

**PLEASE ANSWER THE REMAINING QUESTIONS *AFTER* YOU HAVE TRIED THE PRODUCTS**

PRODUCT CODE

..........................

4. Was there anything you particularly <u>liked</u> about this product?

.................................................
.................................................
.................................................

5. Was there anything you particularly <u>disliked</u> about this product?

.................................................
.................................................
.................................................

6. How would you rate the <u>effectiveness</u> of this product for moisturising your skin?
- Very good  1
- Good  2
- Poor  3
- Very poor  4

7. How would you rate the <u>texture</u> of the product?
- Much too thick  1
- Slightly too thick  2
- Neither too thick nor too runny  3
- Slightly too runny  4
- Much too runny  5

8. How easy was it to apply the cream into your skin?
Very easy...............................1
Quite easy..............................2
Quite difficult.........................3
Very difficult..........................4

9. How well did your skin absorb the cream?
Very easily.............................1
Quite easily............................2
With some difficulty....................3
With much difficulty....................4

10. Did the cream leave any residue on your skin?
Very greasy residue.....................1
A little greasy residue.................2
No residue..............................3

11. How would you describe the sensation left by the cream?
Very refreshed..........................1
Quite refreshed.........................2
A little less refreshed.................3
Much less refreshed.....................4

12. How did this cream feel to use
Very pleasant...........................1
Quite pleasant..........................2
Quite unpleasant........................3
Very Unpleasant.........................4

13. Did you experience any skin irritation with this cream?
Yes.....................................1
No......................................2

14. If you experienced any problems can you describe them?
..................................................
..................................................
..................................................

15. Taking everything into account what is your overall opinion of this cream in terms of its pleasantness to use?
Very good...............................1
Good....................................2
Reasonable..............................3
Poor....................................4
Very Poor...............................5

Questionnaire - Part 1B
CREAMS H and C

PRODUCT CODE
........................

4. Was there anything you particularly liked about this product?
..................................................
..................................................
..................................................

5. Was there anything you particularly disliked about this product?
..................................................
..................................................
..................................................

6. How would you rate the effectiveness of this product for moisturising your skin?
Very good...............................1
Good....................................2
Poor....................................3
Very poor...............................4

7. How would you rate the texture of the product?
Much too thick..........................1
Slightly too thick......................2
Neither too thick nor too runny.........3
Slightly too runny......................4
Much too runny..........................5

8. How easy was it to apply the cream into your skin?
Very easy...............................1
Quite easy..............................2
Quite difficult.........................3
Very difficult..........................4

9. How well did your skin absorb the cream?
Very easily ............................................. 1
Quite easily ........................................... 2
With some difficulty .............................. 3
With much difficulty ............................. 4

10. Did the cream leave any residue on your skin?
Very greasy residue ............................. 1
A little greasy residue .......................... 2
No residue ............................................ 3

11. How would you describe the sensation left by the cream?
Very refreshed ..................................... 1
Quite refreshed .................................... 2
A little less refreshed .......................... 4
Much less refreshed ............................

12. How did this cream feel to use?
Very pleasant ....................................... 1
Quite pleasant ..................................... 2
Quite unpleasant ................................. 3
Very Unpleasant .................................. 4

13. Did you experience any skin irritation with this cream?
Yes ........................................................

No .......................................................... 2

14. If you experienced any problems can you describe them?
..............................................................
..............................................................

15. Taking everything into account what is your overall opinion of this cream in terms of its pleasantness to use?
Very good ............................................. 1
Good ..................................................... 2
Reasonable .......................................... 3
Poor ...................................................... 4
Very Poor ............................................. 5

**PLEASE ANSWER THE FINAL QUESTION *AFTER* YOU HAVE TRIED BOTH THE CREAMS**

17. Overall, which of the two creams would you prefer to use on a daily basis?

Product C ........................................... 1

Product H ...........................................

The following Table (Table 2) provides a summary of the unique combined benefits of the skin barrier repair composition of the present invention. It will be noted that the skin barrier repair composition of the present invention delivers all the ideal benefits whilst eliminating the drawbacks associated with previous skin care formulations.

TABLE 2

| Desirable all round performance - The Ideal | Previously available skin care formulations | The skin barrier repair composition of the present invention |
| --- | --- | --- |
| Encourages Compliance Pleasant to use Readily absorbed No unpleasant residue | No (Barrier creams and Emollients in general e.g. Aqueous cream BP, and a marketed 10% Lactobionate cream) | Yes |
| Effective Therapeutic Delivery and Effects Fast Acting Sustained low pH reduction (12 hours) Sustained Protease Inhibition (12 hours) Twice-a-day dosing ideal | No (Existing formulation technology e.g. marketed 10% Lactobionate) | Yes |
| No Unpleasant Sensation: In-Use and Post-Use Pain Stinging Burning etc. | No (Proven issue with Lactate to deliver the comparable therapeutic benefits) | Yes |
| Antibacterial Activity to Prevent Infection | No | Yes |

Example 7

A Comparison of the Skin Surface pH-Modifying Effects of the New Zinc Lactobionate Test Cream of the Invention with Emollients Currently Marketed in Europe and Asia for Dry, Eczema-Prone Skin Summary Aim: To determine whether a new emollient cream designed to support the skins natural acidic pH (the intervention) can lower skin surface pH in people with atopic dermatitis and compare its effect on pH to a panel of reference emollient creams currently marketed in Europe and Asia for dry, eczema-prone skin.

Method: A single open-application test, wherein eight treatment sites, four per forearm in each participant, were treated with the test cream, 1 no treatment control, and 6 reference creams. After baseline measurements of skin surface pH, 1-fingertip unit of the test/reference creams was applied to each of the relevant treatment sites selected at random. Following treatment, measurement of skin surface pH was conducted at timed intervals (3, 6, 12 and 24 hours post-product application).

Main Findings: The test cream significantly reduced skin surface pH by between 0.7-1.2 units for at least 12 hours following a single application compared to a no treatment control site. Compared to a panel of 6 reference emollient creams marketed for the relief of dry skin in atopic dermatitis patients, the test cream was the only product capable of sustaining pH reduction in excess of 0.5 units for more than 3 hours.

Conclusion: The new emollient cream uniquely supports the skins naturally acidic surface pH by maintaining skin surface pH in atopic dermatitis patients below pH 4.5 for more than 12 hours.

Aim and Objectives

To determine whether a new emollient cream designed to support the skins natural acidic pH can strengthen the skin barrier.

Research Question: Does topical application of the test cream reduce skin surface pH and if so for how long following application is pH significantly decreased?

Hypothesis: The test cream significantly reduces skin surface pH following a single application.

Objectives: To determine the effect of the test cream on skin surface pH and compare its effect to a panel of emollient creams.

Materials and Methods

Participants

A single cohort of 10 volunteers with atopic dermatitis (AD) were recruited. Recruitment was open to male and female volunteers, who were recruited on a first come first served basis, assuming they met the specified criteria. Inclusion criteria included having a self-reported recent history of AD defined by the UK working party diagnostic criteria and being aged 18 years and over. Exclusion criteria included: currently undergoing, or requiring, active drug treatment for AD; a known allergy/hypersensitivity to any of the excipients of the trial preparations; use of topical products (such as spray tan, emollient cream etc.) and/or abrasive cleansers/treatments (scrubs, bleach etc.) on the test sites for 1 week prior to and throughout the study (excluding the test products); dermatitis, acne, suntan, hyperpigmentation, multiple nevi, tattoos, blemishes or dense body hair in the test areas; a condition that in the opinion of the investigator contradicts participation in the study; use of any medication that could interfere with the trial aim (e.g. corticosteroids, calcineurin inhibitors, methotrexate) 6 months prior to the start of the study treatment and throughout the study; current participation in an interventional clinical. Informed consent was obtained from each participant. All participants received remuneration appropriate for their involvement. The University of Sheffield Research Ethics Committee (UREC) approved the study, under the project reference 017681.

Test Design

The forearms (volar face) were divided into 4 test sites (4×5 cm) each. Each test site received a single 100 µl application of either the test cream, Aquamax cream, Cetraben cream, Aqueous cream, Atopiclair cream, Basic Aqua cream, Cetaphil Restoraderm Body Moisturizer or no treatment (see table for ingredients). Randomized site allocation was utilized to minimize site-dependent effects using a randomization list generated at www.randonsation.com. Product identities were concealed from the investigator and participant by assigning each a letter code from A-G. The biophysical properties of the test sites were determined before and at set time points after treatment application. Participants were asked to refrain from washing the test sites until completion of the study.

| Name | Code | Manufacturer | Ingredients |
|---|---|---|---|
| Test cream | C | Hyphens Pharma | Water, Hydrogenated Polydecene, Propylene Glycol, Lactobionic Acid, Behenyl Alcohol, Polyacrylate-1 Cross-polymer, PEG-20 Methyl Glucose Sesquistearate, Aluminum Starch Octenylsuccinate, Methyl Glucose Sesquistearate, Myristyl Alcohol, PVP, Phenoxyethanol, Sodium Chloride, Citric Acid, Xanthan Gum, Zinc Oxide, Ethylhexylglycerin |
| Aquamax cream | E | Intapharm Laboratories | Purified water, White soft paraffin, Cetostearyl alcohol, Liquid paraffin, Polysorbate 60, Phenoxyethanol |
| Cetraben cream | F | Thornton & Ross Ltd | White Soft Paraffin, Light Liquid Paraffin, Emulsifying wax BP, Cetyl Stearyl Alcohol BP, Glycerin, Butylparaben, Methylparaben (E218), Ethylparaben (E214), Propylparaben (E216), Phenoxyethanol BP, Citric Acid, Purified Water. |
| Aqueous cream | A | Numark | Emulsifying Ointment 30% w/w (the ingredients of which are cetostearyl alcohol, sodium lauryl sulfate, liquid parafin and white soft parrafin), phenoxyethanol and purified water. |
| Atopiclair cream | B | Menarini | Aqua, Ethylhexyl Palmitate, *Butyrospermum Parkii* Butter, Pentylene Glycol, Arachidyl Alcohol, Behenyl Alcohol, Arachidyl Glucoside, Butylene Glycol, Glyceryl Stearate, Glycyrrhetinic Acid, Capryloyl Glycine, Bisabol, Tocopheryl Acetate, PEG-100 Stearate, Carbomer, Ethylhexylglycerin, Piroctone Olamine, Sodium Hydroxide, Allantoin, DMDM Hydantoin, Sodium Hyaluronate, *Vitis Vinifera* Seed Extract, Disodium EDTA, Ascorbyl Tetraisopalmitate, Propyl Gallate, Telmesteine |
| Basic Aqua cream | D | ICM Pharma | Purified Water, White Soft Paraffin, Cetosteary1 Alcohol, Ceteareth-20, Liquid Paraffin, Phenoxyethanol |
| Cetaphil Restoraderm body moisturizer | G | Galderma | Aqua, Glycerin, Caprylic/Capric Triglyceride, Helianthus Annus Seed Oil, Pentylene Glycol, *Butyrospermum Parkii* Butter, Cyclopentasiloxane, Cetearyl Alcohol, Sorbitol, Behenyl Alcohol, Glyceryl Stearate, Allantoin, Arginine, Caprylyl Glycol, Ceteareth-20, Cetyl Alcohol, Citric Acid, Dimethiconol, Disodium EDTA, Disodium Ethylene Dicocamide PEG-15 Disulfate, Glyceryl Stearate Citrate, Hydroxypalmitoyl Sphinganine, Niacinamide, Panthenol, Sodium Hyaluronate, Sodium PCA, Sodium Polyacrylate, Tocopheryl Acetate |

Test cream C comprised:
5% w/w lactobionic acid and zinc lactobionate,
20% w/w propylene glycol, and
1% w/w tetradecanol,
and had a pH in the range 3.0-3.5.

Biophysical Measurements

Skin surface pH was measured using a Skin-Surface-pH Meter PH905 (CK electronic GmbH, Cologne, Germany). All assessments were performed in a room maintained at 21±2° C. and 38-50% relative humidity according to published guidelines.[25] All test sites were acclimatised to room conditions for 20 minutes before each assessment.

Visual Scoring of Dryness and Redness

Visual dryness and redness was scored by 2 experienced graders independently using the overall dry skin score (ODS) for dryness where 0 is no dryness and 4 is marked dryness (skin dominated by large scales, advanced roughness, redness present, eczematous changes and cracks) and a 4-point scale for redness from 0 (no redness) to 3 (strong erythema—marked erythema). Scoring was conducted before product application and 24 hours following product application.

Sensory Scoring of Stinging and Burning

Participants were asked to score the sensation of burning/stinging immediately after product application and again 24 hours after product application using a 4-point scale from 0 (no burning or stringing) to 3 (severe burning and/or stinging sensation).

Statistical Analysis

All data were analysed using Prism 7 (GraphPad Software, La Jolla, USA). The significance threshold was $p<0.05$. Results are presented as mean±standard error of the mean (SEM). The data pertaining to the primary (change in skin-surface pH from baseline) outcome was reviewed for normality and transformed as necessary before significance testing at each time-point using a repeated-measures one-way analysis of variance (ANOVA). Significant differences between pairs of the test treatments were identified using Dunnett's post-test. The study was powered (80%) to detect differences in skin-surface-pH of 0.5 units (sample size The visual and sensory scores were summarized without further statistical analysis.

Results

A total of 11 volunteers consented to take part in the study, 10 of which met the inclusion and exclusion criteria. The remaining 1 participant did not meet the UK working party diagnostic criteria and was therefore classed as a screening failure.

The demographic characteristics of the 10 included participants are presented in the table. All 10 participants met the UK working party definition of having atopic dermatitis but were not currently undergoing active drug (i.e. anti-inflammatory agent) treatment. As per protocol the participants refrained from using emollient products on the test sites for 1 week prior to the first study visit and refrained from washing the test sites from 12 hours before the start of the test until after the final measurements were taken.

| Demographic | Included participants (n = 10) |
|---|---|
| Age | 32 ± 10 (range 21-51) |
| Sex: | |
| Male | 3 |
| Female | 7 |
| Ethnicity: | |
| White - British | 8 |
| White - other | 1 |
| Mixed - any other mixed background | 1 |
| Fitzpatrick skin type | 2 (range 2-4) |
| Atopic Dermatitis: | 10/10 (100%) |
| History of involvement of the skin creases | 9/10 (90%) |
| Personal history of asthma or hay fever | 4/10 (40%) |
| History of general dry skin in the past year | 10/10 (100%) |
| Visible flexural eczema | 10/10 (100%) |
| Onset under the age of 2 years | 8/10 (80%) |

All 10 participants completed the study in accordance with the protocol (no protocol deviations). According to a randomization list, the 7 investigational products were each applied to a separate single 4×5 cm test area on the volar forearm to avoid site dependent affects. Owing to the large number of treatment sites (8) in a relatively small cohort of participants (10), it was not possible to balance the number of times each treatment was applied at each test site. As such, based on previous data demonstrating the differences in skin surface pH occurring down the volar face of the forearm, the subsequent data are presented as change relative to baseline measurements.

No adverse events occurred during the conduct of the study.

The effect of a single application of the investigational products on skin surface pH (primary outcome) is summarised in FIGS. 9-10 and the table below.

| Parameter | \multicolumn{8}{c}{Skin-surface-pH by treatment} |
|---|---|---|---|---|---|---|---|---|

| Parameter | A | B | C | D | E | F | G | NTC |
|---|---|---|---|---|---|---|---|---|
| Baseline: | | | | | | | | |
| Mean | 4.68 | 4.69 | 4.95 | 4.99 | 4.89 | 4.62 | 4.81 | 5.05 |
| SD | 0.59 | 0.52 | 0.66 | 0.63 | 0.67 | 0.58 | 0.64 | 0.83 |
| Min | 3.73 | 3.99 | 4.22 | 4.18 | 4.15 | 3.88 | 4.03 | 4.21 |
| Max | 5.83 | 5.74 | 6.40 | 6.25 | 6.46 | 5.82 | 6.12 | 7.06 |
| T = 3: | | | | | | | | |
| Mean | 5.01 | 5.17 | 3.74 | 4.95 | 4.71 | 4.42 | 5.23 | 5.07 |
| SD | 0.47 | 0.32 | 0.12 | 0.49 | 0.37 | 0.46 | 0.34 | 0.80 |
| Min | 4.39 | 4.63 | 3.47 | 4.30 | 4.22 | 3.59 | 4.77 | 4.22 |
| Max | 5.81 | 5.63 | 3.90 | 5.81 | 5.42 | 5.11 | 5.72 | 6.90 |
| T = 6: | | | | | | | | |
| Mean | 4.76 | 4.93 | 4.01 | 4.91 | 4.75 | 4.40 | 5.17 | 4.93 |
| SD | 0.38 | 0.32 | 0.15 | 0.52 | 0.49 | 0.47 | 0.47 | 0.73 |
| Min | 3.90 | 4.22 | 3.79 | 4.15 | 4.14 | 3.80 | 4.44 | 4.02 |
| Max | 5.17 | 5.36 | 4.29 | 5.72 | 5.72 | 5.23 | 5.74 | 6.37 |
| T = 12: | | | | | | | | |
| Mean | 4.82 | 4.86 | 4.27 | 4.98 | 4.74 | 4.51 | 5.09 | 4.93 |
| SD | 0.43 | 0.39 | 0.24 | 0.58 | 0.53 | 0.41 | 0.52 | 0.64 |
| Min | 4.07 | 4.32 | 4.05 | 4.24 | 4.12 | 3.92 | 4.22 | 4.21 |
| Max | 5.34 | 5.43 | 4.90 | 5.86 | 5.64 | 5.19 | 5.81 | 6.14 |
| T = 24: | | | | | | | | |
| Mean | 4.59 | 4.76 | 4.64 | 4.86 | 4.72 | 4.50 | 4.73 | 4.82 |
| SD | 0.43 | 0.37 | 0.34 | 0.42 | 0.41 | 0.42 | 0.49 | 0.52 |
| Min | 3.90 | 4.23 | 4.17 | 4.26 | 4.22 | 3.94 | 4.02 | 4.16 |
| Max | 5.22 | 5.43 | 5.32 | 5.55 | 5.47 | 5.29 | 5.55 | 5.79 |

The eight treatment conditions were found to bring about statistically significant changes in skin surface pH when assessed using a repeated measures one-way ANOVA at each time point (log transformed data to normalise variance and distribution). As can be seen in FIG. 9, product C induces the greatest changes in skin surface pH, achieving a mean reduction of −1.22±0.22 units after 3 hours, −0.94±19 after 6 hours and −0.68±0.17 after 12 hours and −0.32±0.12 after 24 hours relative to baseline measurements. The reduction in skin surface pH brought about by product C is significantly different from the no treatment control 3, 6 and 12 hours after application (Dunnet's post-test). The only other product to reduce skin surface pH significantly (against the no treatment control) is product F, which brings surface pH down by only −0.20±0.07 units 3 hours after application. At all other time points the change in skin surface pH brought about by product F is comparable to the no treatment control (NTC). Three products, A, B and G, transiently increased skin surface pH compared to baseline measurements, by 0.33±0.09, 0.49±0.12 and 0.42±0.12 respectively. Of these products, A has previously been reported to elevate skin surface pH with sodium lauryl sulphate implicated as the source of its alkalinizing effects. Compared to the no treatment control the increase in skin surface pH was significant at 3 hours for A, B and C, at 6 hours for G only, at 12 hours for B and G and at 24 hours post-treatment for B. Products D and E appeared to exert no effects on skin surface pH, being comparable to the no treatment control throughout the experiment. Interestingly D and E are both reformulations of A without the sodium lauryl sulphate further supporting the role of this surfactant in mediating the increased skin surface pH brought about by A.

With respect to visual skin dryness, only 2 test sites overall, 1 in participant 02 and 1 in participant 04 exhibited dryness at baseline (see table). Treatment resulted in the resolution of skin dryness in participant 02 where product F was applied, but not for participant 04 where product D was applied at the site in question. Only one site in one participant (participant 02) exhibited an increase in dryness (of 0.5 units) where product A was applied. Due to the absence of pre-existing dryness at the test sites no appraisal of the moisturizing potential of the products could be made. This is not an unexpected outcome, given that the forearm is not a site typically afflicted by dryness.

In terms of product tolerability, no burning or stinging upon site application was reported immediately after application or 24 hours post-application for any of the treatment conditions (Table 6). No significant changes in skin redness were also observed (Table 7), suggesting that all 7 products tested are tolerated in AD patients following a single application under the conditions tested.

| | Visual skin dryness by treatment | | | | | | | |
|---|---|---|---|---|---|---|---|---|
| Parameter | A | B | C | D | E | F | G | NTC |
| Baseline: | | | | | | | | |
| Median | 0 | 0 | 0 | 0 | 0 | 0 | 0 | 0 |
| Min | 0 | 0 | 0 | 0 | 0 | 0 | 0 | 0 |
| Max | 0 | 0 | 0 | 1 | 0 | 0.5 | 0 | 0 |
| T = 24: | | | | | | | | |
| Median | 0 | 0 | 0 | 0 | 0 | 0 | 0 | 0 |
| Min | 0 | 0 | 0 | 0 | 0 | 0 | 0 | 0 |
| Max | 0.5 | 0 | 0 | 1 | 0 | 0 | 0 | 0 |
| Change from baseline: | | | | | | | | |
| Median | 0 | 0 | 0 | 0 | 0 | 0 | 0 | 0 |
| Min | 0 | 0 | 0 | 0 | 0 | −0.5 | 0 | 0 |
| Max | 0.5 | 0 | 0 | 0 | 0 | 0 | 0 | 0 |
| No. Increased | 1 | 0 | 0 | 0 | 0 | 0 | 0 | 0 |
| No. Decreased | 0 | 0 | 0 | 0 | 0 | 1 | 0 | 0 |

| | Burning and stinging sensation by treatment | | | | | | | |
|---|---|---|---|---|---|---|---|---|
| Parameter | A | B | C | D | E | F | G | NTC |
| Baseline: | | | | | | | | |
| Median | 0 | 0 | 0 | 0 | 0 | 0 | 0 | 0 |
| Min | 0 | 0 | 0 | 0 | 0 | 0 | 0 | 0 |
| Max | 0 | 0 | 0 | 0 | 0 | 0 | 0 | 0 |
| T = 24: | | | | | | | | |
| Median | 0 | 0 | 0 | 0 | 0 | 0 | 0 | 0 |
| Min | 0 | 0 | 0 | 0 | 0 | 0 | 0 | 0 |
| Max | 0 | 0 | 0 | 0 | 0 | 0 | 0 | 0 |

| | Treatment | | | | | | | |
|---|---|---|---|---|---|---|---|---|
| Parameter | A | B | C | D | E | F | G | NTC |
| Baseline: | | | | | | | | |
| Median | 0 | 0 | 0.125 | 0.25 | 0.125 | 0 | 0 | 0.125 |
| Min | 0 | 0 | 0 | 0 | 0 | 0 | 0 | 0 |
| Max | 0.75 | 0.5 | 0.5 | 0.5 | 0.5 | 0.75 | 0.5 | 0.5 |
| T = 24: | | | | | | | | |
| Median | 0 | 0 | 0 | 0 | 0 | 0 | 0 | 0 |
| Min | 0 | 0 | 0 | 0 | 0 | 0 | 0 | 0 |
| Max | 0.25 | 0 | 0 | 0.5 | 0 | 0.5 | 0 | 0 |
| Change from baseline: | | | | | | | | |
| Median | 0 | 0 | −0.125 | 0 | −0.125 | 0 | 0 | −0.125 |
| Min | −0.5 | −0.5 | −0.5 | −0.5 | −0.5 | −0.5 | −0.5 | −0.5 |
| Max | 0 | 0 | 0 | 0 | 0 | 0.5 | 0 | 0 |
| No. Increased | 0 | 0 | 0 | 0 | 0 | 1 | 0 | 0 |
| No. Decreased | 4 | 4 | 5 | 4 | 5 | 4 | 4 | 5 |

Conclusions

The test cream significantly reduced skin surface pH by between 0.7-1.2 units for at least 12 hours following a single application compared to a no treatment control site. As a result, skin surface pH was maintained below pH 4.5 for more than 12 hours. Compared to a panel of 6 reference emollient creams marketed for the relief of dry skin in AD patients, the test cream was the only product capable of sustaining pH reduction in excess of 0.5 units for more than 3 hours. In the absence of skin dryness the potential of the test products to moisturise the skin could not be assessed. All products tested were tolerated, with no signs of burning, stringing or redness.

Example 8

The Effect of the Invention on Skin Hydration in Atopic Dermatitis Patients

Aim

To determine whether the invention can increase skin hydration after a single application in patients with atopic dermatitis who are prone to skin dryness.

Method

A cohort of 10 adult volunteers with atopic dermatitis, according to the UK working party diagnostic criteria, were recruited. Informed consent was obtained from all participants and the study design was approved by the University of Sheffield Research Ethics Committee. In each participant a single application (100 μl) of the invention/the test cream was applied to a 20 cm$^2$ area of skin. Hydration was measured using a corneometer (capacitance method) before and 3 hours after application.

Results

A single application of the test cream brought about a change in capacitance of 3.9±1.8 (arbitrary capacitance units), demonstrating its capacity to increase skin water/hydration levels (see FIG. 11).

The invention claimed is:

1. A composition for topical administration to an external body surface of a subject comprising:
    a polyhydroxy acid and a zinc salt of its conjugate base, wherein the polyhydroxy acid is selected from the group consisting of lactobionic acid, gluconolactone, a combination of lactobionic acid and gluconolactone, and derivatives thereof,
    a partition coefficient enhancer selected from the group consisting of propylene glycol, butylene glycol, pentylene glycol, hexylene glycol, 1,5 pentane diol, and combinations thereof, wherein the partition coefficient enhancer is at 15 30% w/w of the composition, and
    a diffusion coefficient enhancer which is selected from a C12 to C14 straight chain fatty acid or a C14 straight chain primary alcohol, wherein the diffusion coefficient enhancer is at 1.0-2.0% w/w of the composition,
    and wherein the composition has a pH in the range consisting of 2.7 to 5.0.

2. The composition according to claim 1, wherein the concentration of partition coefficient enhancer is 15-25, 17-23, 18-22, or about 20% w/w of the composition.

3. The composition according to claim 1, wherein the partition coefficient enhancer is propylene glycol.

4. The composition according to claim 1, wherein the concentration of diffusion coefficient enhancer is 1.2-1.8 or about 1.5% w/w of the composition.

5. The composition according to claim 1, wherein the diffusion coefficient enhancer is 1-tetradecanol.

6. The composition according to claim 1, wherein the concentration of polyhydroxy acid and the zinc salt of its conjugate base is 2.0-10.0% w/w of the composition.

7. The composition according to claim 1, wherein the concentration of polyhydroxy acid and the zinc salt of its conjugate base is greater than or equal to 2.5, 3.0, 3.5, 4.0, 4.5 or 5.0% w/w of the composition, and is less than or equal to 9.5, 9.0, 8.5, 8.0 or 7.5% w/w of the composition.

8. The composition according to claim 1, wherein the concentration of polyhydroxy acid is from 3.0 to 6.5, or from 3.5 to 6.0, or from 4.0 to 5.5 or is about 5 w/w of the composition.

9. The composition according claim 1, wherein the polyhydroxy acid is lactobionic acid.

10. The composition according to claim 1, wherein the zinc salt of the conjugate base used in the composition is formed from zinc oxide (ZnO).

11. The composition according to claim 1, wherein the composition further comprises from 10.0 to 30.0, 10.0 to 25.0, 10.0 to 20.0, 12.0 to 16.0 or about 14% w/w of an emollient.

12. The composition of claim 11, wherein the emollient is a high molecular weight hydrocarbon, selected from the group consisting of mineral oil, petrolatum, paraffin, and mixtures thereof.

13. The composition of claim 11, wherein the emollient is selected from the group consisting of hydrogenated polydecene, hydrogenated didecene, hydrogenated polyisobutene and mixtures thereof.

14. The composition of claim 1, wherein the pH of the composition is in the range of 3.0 to 4.5, or is in the range of 3.0 to 4.0, or is in the range of 3.0 to 3.5, or is about 3.2.

15. The composition of claim 1, wherein the composition comprises a further acid to modulate the pH of the composition.

16. The composition of claim 1, wherein the composition further comprises 3.0-12.0, 4.0-12.0, 6.0-10.0, 8.0-9.0, or about 8.5% w/w of surfactant.

17. The composition of claim 16, wherein the surfactant is a surfactant system comprising Glucate SS Emulsifier (methyl glucose sesquistearate) and Glucamate SSE-20 Emulsifier (PEG-20 methyl glucose sesquistearate), optionally further comprising glyceryl stearate.

18. The composition of claim 1, further comprising a ceramide.

19. The composition of claim 18, further comprising a cholesterol and at least one additional fatty acid.

20. The composition of claim 19, wherein the ceramide, the cholesterol, and the at least one additional fatty acid is approximately in a 3:1:1 weight ratio.

21. The composition of claim 20, wherein the ceramide, cholesterol and the at least one additional fatty acid comprises ceramide, cholesterol and linoleic acid in approximately a 3:1:1 weight ratio.

22. The composition of claim 1, further comprising one or more of a stabilizer, a preservative or a salt.

23. The composition according to any of the preceding claims, further comprising one or more pharmaceutically acceptable excipient, carrier, diluent or vehicle.

24. A composition for topical administration to an external body surface of a subject comprising an aqueous-glycol phase comprising:
    a polyhydroxy acid and a zinc salt of its conjugate base at 4.0-6.0% w/w, wherein the polyhydroxy acid is selected from the group consisting of lactobionic acid, gluconolactone (gluconic acid), a combination of lactobionic acid and gluconolactone (gluconic acid), and derivatives thereof,
    a partition coefficient enhancer selected from the group consisting of propylene glycol, butylene glycol, pentylene glycol, hexylene glycol, 1,5 pentane diol, propylene carbonate, dipropylene glycol, diethylene glycol monoethyl ether, N-methyl pyrrolidone and a combination thereof at 18.0-22.0% w/w of, and water,
    and an oil phase comprising:
    a diffusion coefficient enhancer which is a C12 to C14 straight chain fatty acid or a C14 straight chain primary alcohol at 1.0-2.0% w/w,
    a second agent as emollient, and a third agent as surfactant,
    wherein % w/w is based on the composition, and wherein the composition has a pH in the range consisting of 3.0 to 3.5.

25. The composition according to claim 24, wherein the polyhydroxy acid and a zinc salt of its conjugate base is lactobionic acid and zinc lactobionate, respectively.

26. The composition according to claim 24, wherein the partition coefficient enhancer is propylene glycol.

27. The composition according to claim 24, wherein the diffusion coefficient enhancer is 1-tetradecanol.

28. The composition according to claim 1, wherein the composition comprises an aqueous-glycol phase and an oil phase.

29. The composition according to claim 1, wherein a single application of the composition to the skin, causes at least a 0.5 pH unit reduction in skin surface pH for at least 3 hours.

30. The composition according to claim 1, for use in therapy.

31. A pharmaceutical formulation comprising a composition according to claim 1, to treat a condition caused by a defective skin barrier or for promoting skin barrier repair.

32. A pharmaceutical formulation comprising a composition according to claim 1, to treat condition selected from eczema, atopic eczema, dermatitis, atopic dermatitis, non-atopic dermatitis, non-atopic eczema, seborrheic eczema, irritant contact dermatitis, allergic contact dermatitis, asteatotic eczema, pruritis, dry skin, sensitive skin, acne, acne scars, dryness of skin, nail and hair, xerosis, ichthyosis, palmar and plantar hyperkeratosis with uneven and rough surface of skin, dandruff, Darier's disease, lichen simplex chronicus, keratosis, pseudofolliculitis barbae, psoriasis, warts, herpes, age spots, lentigines, melasmas, blemished skin, mottled skin, hyperkeratosis, hyperpigmented skin, stretch marks, thinning of nail plate and hair fragility and splitting of nail and hair, skin wounds, diseases or conditions of oral, gum and vaginal mucosa, burns, and abraded skin or any condition that skin has been damaged.

33. A pharmaceutical formulation comprising a composition according to claim 1, to treat condition selected from eczema, atopic eczema, dermatitis, atopic dermatitis, non-atopic eczema, non-atopic dermatitis, seborrheic eczema, irritant contact dermatitis, allergic contact dermatitis, asteatotic eczema, pruritis, acne, dry skin, or sensitive skin.

34. The composition of claim 22, wherein the preservative comprises phenoxyethanol.

* * * * *